US008975067B2

(12) United States Patent
Foltz et al.

(10) Patent No.: US 8,975,067 B2
(45) Date of Patent: *Mar. 10, 2015

(54) SELF-CONTAINED STERILIZATION INDICATORS INCLUDING A NEUTRALIZER FOR RESIDUAL OXIDIZING STERILANT

(75) Inventors: William E. Foltz, Cottage Grove, MN (US); Francois Ahimou, Woodbury, MN (US); G. Marco Bommarito, Stillwater, MN (US); Robert A. Asmus, Hudson, WI (US); Louis C. Haddad, Mendota Heights, MN (US); Tushar A. Kshirsagar, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/995,524

(22) PCT Filed: Dec. 20, 2011

(86) PCT No.: PCT/US2011/066079
§ 371 (c)(1),
(2), (4) Date: Jun. 19, 2013

(87) PCT Pub. No.: WO2012/088064
PCT Pub. Date: Jun. 28, 2012

(65) Prior Publication Data
US 2013/0273593 A1 Oct. 17, 2013

Related U.S. Application Data

(60) Provisional application No. 61/426,291, filed on Dec. 22, 2010.

(51) Int. Cl.
*C12M 3/00* (2006.01)

(52) U.S. Cl.
USPC ................................. 435/287.4; 435/287.6

(58) Field of Classification Search
USPC ..................... 435/287.4, 287.6, 31
IPC .................. C12Q 1/22; C12M 23/32
See application file for complete search history.

(56) References Cited

U.S. PATENT DOCUMENTS

| | | | |
|---|---|---|---|
| 4,368,081 A * | 1/1983 | Hata et al. ................... 134/2 |
| 4,643,876 A | 2/1987 | Jacobs et al. |
| 4,756,882 A | 7/1988 | Jacobs et al. |
| 4,863,688 A | 9/1989 | Schmidt et al. |
| 5,073,488 A * | 12/1991 | Matner et al. ................. 435/31 |
| 5,252,484 A | 10/1993 | Matner et al. |
| 5,405,580 A | 4/1995 | Palmer |
| 5,482,171 A | 1/1996 | Palmer |
| 5,486,459 A | 1/1996 | Burnham et al. |
| 5,500,184 A | 3/1996 | Palmer |
| 5,552,320 A * | 9/1996 | Smith ...................... 435/287.4 |
| 5,788,925 A | 8/1998 | Pai et al. |
| 5,795,730 A | 8/1998 | Tautvydas |
| 5,801,010 A * | 9/1998 | Falkowski et al. ............ 435/31 |
| 5,856,118 A | 1/1999 | Dalmasso |
| 5,866,356 A | 2/1999 | Albert et al. |
| 5,872,004 A | 2/1999 | Bolsen |
| 5,942,438 A | 8/1999 | Antonoplos et al. |
| 6,187,555 B1 | 2/2001 | Tautvydas |
| 6,193,931 B1 | 2/2001 | Lin et al. |
| 6,355,448 B1 | 3/2002 | Foltz et al. |
| 6,436,659 B1 | 8/2002 | Hui et al. |
| 6,458,554 B1 * | 10/2002 | Hui et al. ..................... 435/31 |
| 6,897,059 B2 * | 5/2005 | Foltz et al. ................ 435/287.6 |
| 6,936,434 B2 | 8/2005 | McDonnell et al. |
| 7,045,343 B2 | 5/2006 | Witcher et al. |
| 7,642,067 B2 | 1/2010 | Song et al. |
| 8,071,362 B2 * | 12/2011 | Franciskovich et al. ... 435/287.1 |
| 8,283,133 B2 * | 10/2012 | Franciskovich et al. ........ 435/31 |
| 2002/0081228 A1 | 6/2002 | Hui et al. |
| 2002/0160440 A1 | 10/2002 | McDonnell et al. |
| 2004/0248235 A1 * | 12/2004 | Foltz et al. ..................... 435/31 |
| 2006/0083657 A1 * | 4/2006 | McDonnell et al. ............ 422/55 |
| 2007/0003995 A1 | 1/2007 | Song et al. |
| 2009/0305334 A1 | 12/2009 | Dallmier et al. |

FOREIGN PATENT DOCUMENTS

| | | |
|---|---|---|
| EP | 0 371 682 | 6/1990 |
| EP | 0 421 760 | 4/1991 |
| EP | 0 638 650 | 2/1995 |
| EP | 1 201 255 | 5/2002 |
| WO | WO 95/21936 | 8/1995 |
| WO | WO 99/62569 | 12/1999 |
| WO | WO 2008/082728 | 7/2008 |
| WO | WO 2008/130802 | 10/2008 |
| WO | WO 2009/052137 | 4/2009 |
| WO | WO 2011/002878 | 1/2011 |
| WO | WO 2012/088048 | 6/2012 |

OTHER PUBLICATIONS

Davies, C.N. et al., "The Separation of Airborne Dust and Particles," *Institution of Mechanical Engineers*, Proceedings (B); vol. 1B, London; 1952; pp. 185-213.
Laurence, D.J.R., "Fluorescence Techniques for the Enzymologist," *Methods in Enzymology*, Colowick and Kaplan, Eds. Academic Press, New York, vol. IV; 1957, pp. 174-212.
Roth, M., "Fluorimetric Assay of Enzymes"; *Methods of Biochemical Analysis*, vol. 17, D. Glick, Ed., Interscience Publishers, New York, 1969, pp. 189-192.
Shafrin, E.G. et al., "Constitutive Relations in the Wetting of Low Energy Surfaces and the Theory of the Retraction Method of Preparing Monolayers"; *The Journal of Physical Chemistry*, vol. 64, No. 5; 1960; pp. 519-524.
Udenfriend, S., "Chapter 9—Fluorescence in Enzymology"; Fluorescence Assay in Biology and Medicine, Academic Press, New York, 1962. pp. 312-348.

* cited by examiner

Primary Examiner — Ralph Gitomer

(57) ABSTRACT

Sterilization indicators that include a neutralizer, such indicators useful for testing the effectiveness of a sterilization procedure by measuring the activity of an active enzyme whose activity is correlated with the survival of microorganisms.

16 Claims, 7 Drawing Sheets

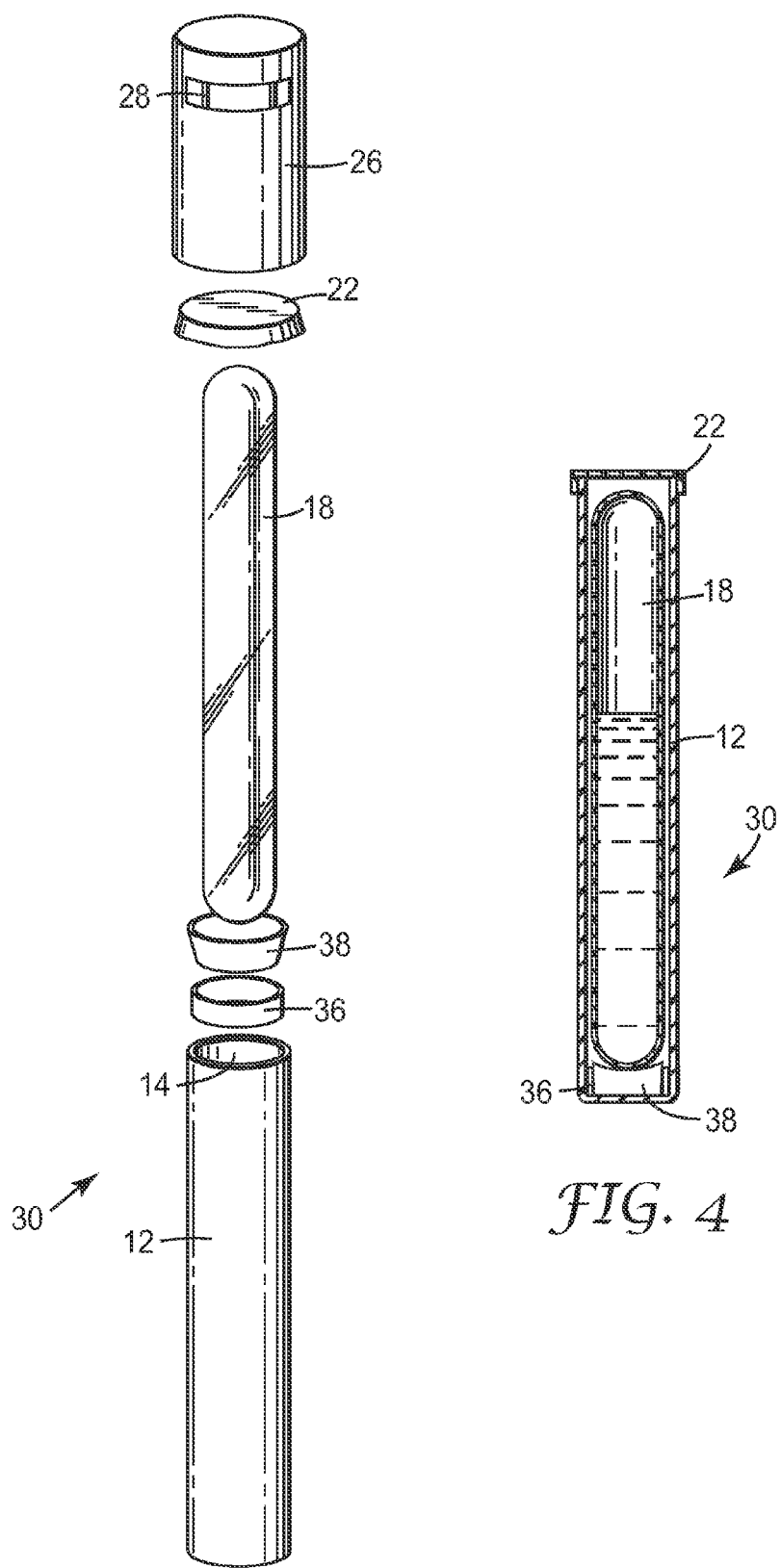

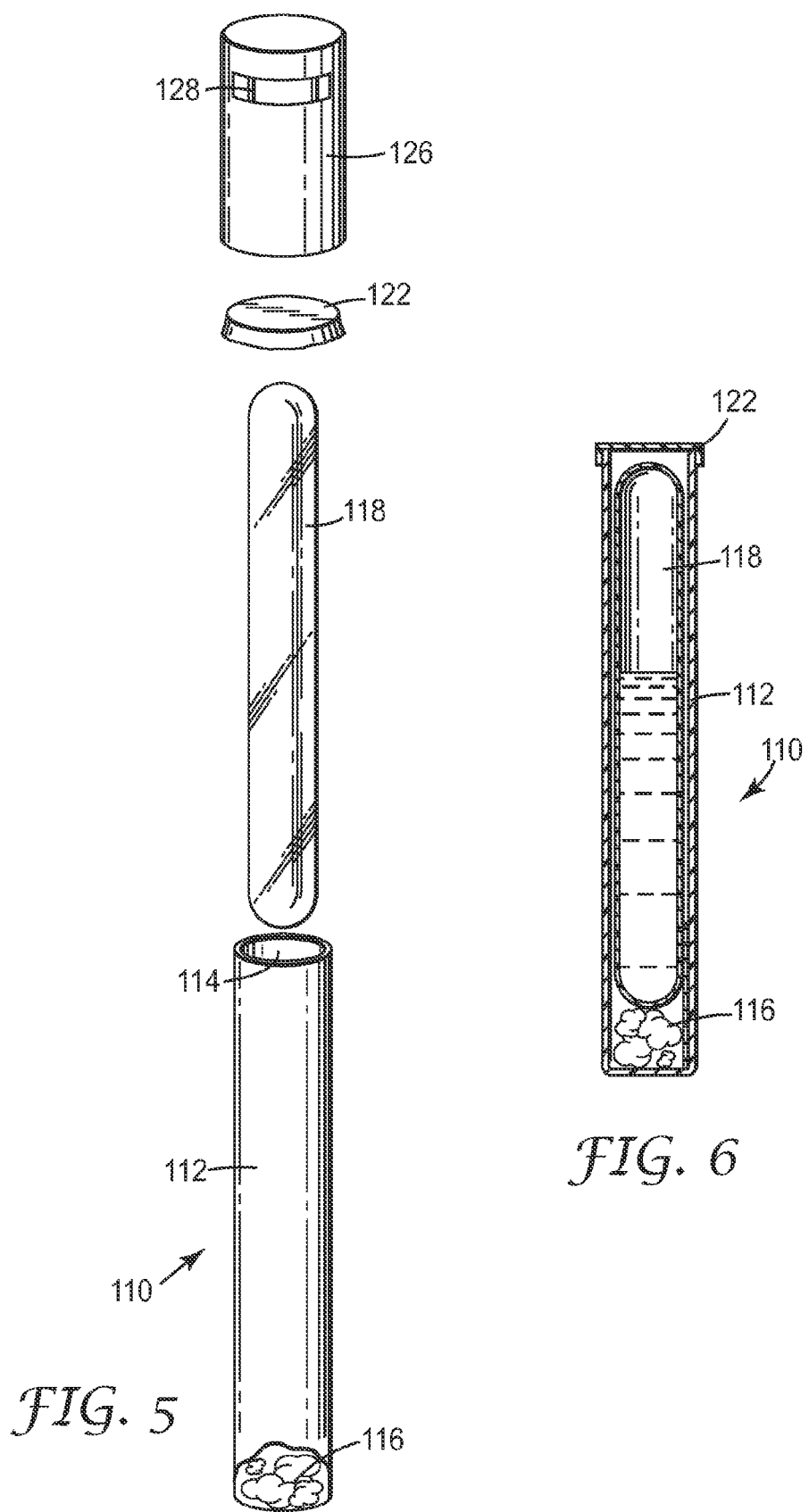

SELF-CONTAINED STERILIZATION INDICATORS INCLUDING A NEUTRALIZER FOR RESIDUAL OXIDIZING STERILANT

CROSS REFERENCE TO RELATED APPLICATION

This application is a national stage filing under 35 U.S.C. 371 of PCT/US2011/066079, filed Dec. 20, 2011, which claims the benefit of U.S. Provisional Patent Application No. 61/426,291, filed Dec. 22, 2010 the disclosure of which is incorporated by reference in their entirety herein.

BACKGROUND

Sterilization indicators (also referred to as biological indicators) provide a means for determining whether a sterilizing machine, such as those used to sterilize surgical instruments in hospitals, is functioning properly and killing microorganisms that are present in the sterilization chamber during a sterilization procedure.

Sterilization indicators are recognized in the art as providing an accurate and precise means for testing the effectiveness of a sterilization procedure. Conventional sterilization indicators gauge the effectiveness of a sterilization procedure by monitoring the survival of a test microorganism contained within the sterilization indicator that is many times more resistant to the sterilization process than most organisms that would ordinarily be present by natural contamination. The sterilization indicator is exposed to a sterilization cycle and then incubated under conditions that will promote the growth of any surviving test microorganisms. If the sterilization cycle fails, the sterilization indicator generates a detectable signal indicating that the biological specimen survived. The detectable signal is commonly an indication such as a color change or the emission of a luminescent or fluorescent signal.

One well-known type of sterilization indicator employs spores from bacteria or fungi, which are very resistant to sterilization, to test the effectiveness of a sterilization procedure. A typical sterilization indicator has an outer container (e.g., tube, sleeve, or ampoule) made of a compressible, plastic material and a sealed inner container (e.g., tube, sleeve, or ampoule) made of a breakable material such as glass. A bacteria impermeable, gas transmissive covering on the outer container allows sterilant to enter the outer container during a sterilization procedure. Live spores on a piece of carrier are located between the walls of the outer container and the inner container. The inner container contains a growth medium that stimulates the growth of live spores. During the sterilization procedure, sterilant enters the outer container through the cap and contacts the spores within the carrier. After the sterilization procedure, the inner container is crushed by compressing the outer container, releasing the growth medium and bringing it into contact with the spores within the carrier. The indicator is then incubated under conditions that stimulate spore growth. If the sterilization procedure is ineffective, surviving spores will grow out and cause a pH indicator in the growth medium to change color, indicating that the sterilization cycle failed to kill the test population of microorganisms and may have failed to kill contaminating microorganisms present in the sterilizer load. Although sterilization indicators that rely on the growth of spores are accurate, they are slow, commonly requiring between 1 and 7 days to provide final results.

In contrast to sterilization indicators that measure spore growth alone, enzyme indicators provide a rapid answer, often in a matter of a few hours. Such indicators measure the effectiveness of a sterilization procedure by measuring the activity of an enzyme whose activity is correlated with the destruction of contaminating microorganisms during a sterilization procedure. The indicators have a compressible outer container, a breakable inner container, and a cap that is bacteria impermeable but gas transmissive. Active enzyme is impregnated on a carrier located between the walls of the outer and inner containers, and a substrate that reacts with the active enzyme is contained within the sealed inner container. During the sterilization procedure the sterilant enters the outer container and contacts the active enzyme within the carrier. After the sterilization procedure, the inner vial is crushed and the enzyme strip is exposed to the substrate and incubated. If the sterilization procedure works properly, the enzyme is inactivated during the procedure and there is no detectable change following incubation. However, if the sterilization procedure is ineffective, the enzyme is not inactivated and will react with the substrate to form a detectable product. The enzyme-substrate product may be detectable as a color change or as a fluorescent or luminescent signal.

Dual rapid-readout indicators are sterilization indicators that test the effectiveness of a sterilization procedure by measuring both enzyme activity and spore growth following exposure to a sterilization procedure. The enzyme system gives a rapid indication of the effectiveness of a sterilization cycle, which is then confirmed by measurement of spore outgrowth over a longer period of time. In a dual rapid-readout indicator, the live spores utilized in the spore outgrowth portion of the indicator may also serve as the source of active enzyme for the enzyme activity portion of the assay. The rapid enzyme test measures the activity of an enzyme that is associated with the spores, and the spores themselves are then incubated to encourage the outgrowth of any spores that survived the sterilization procedure. 3M ATTEST 1291 and 1292 Rapid-readout Biological Indicators, available from 3M Company, St. Paul, Minn., are dual rapid-readout indicators that test the effectiveness of a sterilization cycle by measuring both the activity of an enzyme associated with *Geobacillus stearothermophilus* (formerly known as *Bacillus stearothermophilis*) spores in the indicator and the survival of the spores themselves.

SUMMARY OF THE DISCLOSURE

The present disclosure relates to sterilization indicators for testing the effectiveness of a sterilization procedure and methods of use. The sterilization indicators of the present disclosure can be indicators that measure spore growth (referred to herein as spore outgrowth indicators), indicators that measure enzyme activity and provide a rapid answer (referred to herein as enzyme-based indicators), or indicators that test the effectiveness of a sterilization procedure by measuring both enzyme activity and spore growth following exposure to a sterilization procedure (also referred to herein as enzyme-based indicators, and more specifically as enzyme-based/spore outgrowth indicators).

In one embodiment, the present disclosure provides a sterilization indicator for testing the effectiveness of a sterilization procedure, wherein the indicator includes: a container having at least one opening to allow an oxidizing sterilant to enter the container during the sterilization procedure; a carrier contained within the container; biological material supported by the carrier, the biological material being correlated with the survival of at least one test microorganism commonly used to monitor the effectiveness of a sterilization procedure, wherein the biological material is inactivated as a result of an effective sterilization procedure, and provides a detectable indication as a result of an ineffective sterilization procedure; wherein one or more components of the sterilization indicator retains residual oxidizing sterilant; a neutralizer disposed within the indicator in an amount effective to neutralize residual oxidizing sterilant, wherein the neutralizer is not an enzyme and not a metal catalyst; and means for forming a detectable indication of the failure of a sterilization procedure. This can be a spore outgrowth indicator (wherein the biological material includes spores, and the detectable indication is a pH indication). Alternatively, it can be an enzyme-based indicator (wherein the biological material includes a source of an active enzyme, and the detectable indication includes a detectable fluorescence, luminescence, and/or chromogenic indication). The enzyme-based indicator can be a dual enzyme-based/spore outgrowth indicator (wherein the biological material includes a source of an active enzyme that is also suitable for a spore outgrowth test, and the detectable indication includes a detectable fluorescence, luminescence, and/or chromogenic indication followed by a pH indication).

In another embodiment, the present disclosure provides a sterilization indicator for testing the effectiveness of a sterilization procedure, wherein the indicator includes: a container having at least one opening to allow an oxidizing sterilant to enter the container during the sterilization procedure; a carrier contained within the container; biological material including a source of an active enzyme, wherein the source of active enzyme is supported by the carrier; wherein the active enzyme has an enzyme activity that is correlated with the survival of at least one test microorganism commonly used to monitor the effectiveness of a sterilization procedure; wherein the source of an active enzyme is inactivated by a sterilization procedure that is lethal to the test microorganism, but wherein the source of an active enzyme is not inactivated by a sterilization procedure that is sublethal to the test microorganism; wherein one or more components of the sterilization indicator retains residual oxidizing sterilant; a neutralizer disposed within the indicator in an amount effective to neutralize residual oxidizing sterilant, wherein the neutralizer is not an enzyme and not a metal catalyst; and means for forming an enzyme-modified product that provides a detectable indication of the failure of a sterilization procedure.

In another embodiment, the present disclosure provides a sterilization indicator for testing the effectiveness of a sterilization procedure, wherein the indicator includes: an outer container having at least one opening to allow sterilant to enter the outer container during the sterilization procedure; a carrier contained within the outer container; biological material including a source of an active enzyme, wherein the source of active enzyme is supported by the carrier; wherein the active enzyme has an enzyme activity that is correlated with the survival of at least one test microorganism commonly used to monitor the effectiveness of a sterilization procedure; wherein the source of an active enzyme is inactivated by a sterilization procedure that is lethal to the test microorganism, but wherein the source of an active enzyme is not inactivated by a sterilization procedure that is sublethal to the test microorganism; wherein one or more components of the sterilization indicator retains residual oxidizing sterilant; a neutralizer disposed within the indicator in an amount effective to neutralize residual oxidizing sterilant, wherein the neutralizer is not an enzyme and not a metal catalyst; and a breakable inner container within the outer container, wherein the inner container: is impermeable to the sterilant used in the sterilization procedure; includes an enzyme substrate; and is adapted so that it may be broken to allow the enzyme substrate to react with active enzyme to form an enzyme-modified product that provides a detectable indication of the failure of a sterilization procedure.

In another embodiment, the present disclosure provides a rapid-readout hydrogen peroxide sterilization indicator for testing the effectiveness of a hydrogen peroxide sterilization procedure, wherein the indicator includes: an outer container having at least one opening to allow hydrogen peroxide sterilant to enter the outer container during the sterilization procedure; a carrier contained within the outer container; biological material including a source of an active enzyme, wherein the source of active enzyme is supported by the carrier; wherein the active enzyme has an enzyme activity that is correlated with the survival of at least one test microorganism commonly used to monitor the effectiveness of a sterilization procedure; wherein the source of an active enzyme is inactivated by a sterilization procedure that is lethal to the test microorganism, but wherein the source of an active enzyme is not inactivated by a sterilization procedure that is sublethal to the test microorganism; wherein one or more components of the sterilization indicator retains residual hydrogen peroxide sterilant; and a breakable inner container within the outer container, wherein the inner container: is impermeable to the hydrogen peroxide sterilant used in the sterilization procedure; includes a mixture including an enzyme substrate and a neutralizer disposed within the indicator in an amount effective to neutralize residual hydrogen peroxide sterilant, wherein the neutralizer is not an enzyme and not a metal catalyst; and is adapted so that it may be broken to allow the enzyme substrate to react with active enzyme to form an enzyme-modified product that provides a detectable indication of the failure of a hydrogen peroxide sterilization procedure, wherein the detectable indication is formed within 8 hours or less.

The present disclosure also provides methods of use. In one embodiment, the present disclosure provides a method for testing the effectiveness of a sterilization procedure, the method including: providing a sterilization indicator including: a container having at least one opening to allow an oxidizing sterilant to enter the container during the sterilization procedure; a carrier contained within the container; biological material supported by the carrier, the biological material being correlated with the survival of at least one test microorganism commonly used to monitor the effectiveness of a sterilization procedure, wherein the biological material is inactivated as a result of an effective sterilization procedure, and provides a detectable indication as a result of an ineffective sterilization procedure; wherein one or more components of the sterilization indicator retains residual oxidizing sterilant; a neutralizer disposed within the indicator in an amount effective to neutralize residual oxidizing sterilant, wherein the neutralizer is not an enzyme and not a metal catalyst; and means for forming a detectable indication of the failure of a sterilization procedure; subjecting the sterilization indicator including biological material to a sterilization procedure; subsequent to sterilization, subjecting the sterilization indicator to a developing procedure to determine whether a detectable indication is present or absent; and correlating the presence of the detectable indication with failure of the sterilization procedure and the absence of the detectable indication with success of the sterilization procedure.

Using an exemplary spore outgrowth sterilization indicator, a method for testing the effectiveness of a sterilization procedure includes: providing a sterilization indicator including: a carrier; biological material including spores, wherein the spores are supported by the carrier; the biological material being correlated with the survival of at least one test microorganism commonly used to monitor the effectiveness of a sterilization procedure, wherein the biological material is inactivated as a result of an effective sterilization procedure, and provides a detectable indication as a result of an ineffective sterilization procedure; wherein one or more components of the sterilization indicator retains residual oxidizing sterilant; and a neutralizer disposed within the indicator in an amount effective to neutralize residual oxidizing sterilant, wherein the neutralizer is not an enzyme and not a metal catalyst; subjecting the sterilization indicator including biological material to a sterilization procedure; subsequent to sterilization, combining the biological material with a growth medium that includes a pH indicator, and incubating the mixture of biological material and growth medium under conditions that stimulate spore growth; determining whether surviving spores, which have a detectable pH signal, are present or absent in the biological material; and correlating the presence of the detectable signal with failure of the sterilization procedure and the absence of the detectable signal with success of the sterilization procedure.

Using an exemplary enzyme-based sterilization indicator, a method for testing the effectiveness of a sterilization procedure includes: providing a sterilization indicator including: a carrier; biological material including a source of an active enzyme, wherein the source of active enzyme is supported by the carrier; wherein the active enzyme has an enzyme activity that is correlated with the survival of at least one test microorganism commonly used to monitor the effectiveness of a sterilization procedure; wherein the source of an active enzyme is inactivated by a sterilization procedure that is lethal to the test microorganism, but wherein the source of an active enzyme is not inactivated by a sterilization procedure that is sublethal to the test microorganism; wherein one or more components of the sterilization indicator retains residual oxidizing sterilant; a neutralizer disposed within the indicator in an amount effective to neutralize residual oxidizing sterilant, wherein the neutralizer is not an enzyme and not a metal catalyst; and an enzyme substrate that reacts with the active enzyme to form an enzyme-modified product, which has a detectable signal, upon failure of a sterilization procedure; subjecting the source of active enzyme to a sterilization procedure; combining the enzyme and the substrate to form an enzyme-modified product; determining whether the enzyme-modified product, which has a detectable signal, is present or absent; and correlating the presence of the detectable signal with failure of the sterilization procedure and the absence of the detectable signal with success of the sterilization procedure. In a particularly preferred embodiment, the sterilization indicator is a dual rapid-readout indicator and the source of active enzyme includes spores of a microorganism that serve as both the source of active enzyme for the enzyme activity test, and the test microorganism for the spore outgrowth test.

Herein, a "porous" carrier means that sterilant can pass through the carrier under normal conditions of sterilization (such conditions are defined by the particular sterilization procedure). A "three-dimensional" porous carrier is one that occupies at least 5% of the volume of a container in which it is located (e.g., the outer container of a two-container device).

Herein, "supported by" the carrier means that the biological material may be disposed on the surface of the carrier (especially, if it is not porous) or distributed within a porous carrier.

Herein, "distributed within" a porous carrier means that the biological material may be uniformly or nonuniformly distributed throughout at least a portion of the volume of a porous carrier (i.e., not only on its surface). "Distributed within" includes distributed throughout (and uniformly distributed throughout) the entire volume of the porous carrier.

Herein, "biological material" refers to the material supported by the carrier that is correlated with the survival of at least one test microorganism, and contributes to the formation of a detectable signal. That is, the biological material is inactivated (e.g., killed) as a result of an effective sterilization procedure, and provides a detectable indication as a result of an ineffective sterilization procedure. The biological material can be spores or other microorganisms that serve as a source of an active enzyme. The source of active enzyme can also be an isolated enzyme.

Herein, a "test microorganism" refers to a microorganism commonly used to monitor the effectiveness of a sterilization procedure, such as *Geobacillus stearothermophilus*.

Herein, in the context of the material of which the carrier is made, the term "hydrophilic" means having a contact angle of zero (i.e., wetted by water). This hydrophobic material can be inorganic, organic, or a combination thereof.

Herein, in the context of the material of which the carrier is made, the term "hydrophobic" means repelling of water, measurable by a non-zero contact angle, as described in E. Sharfrin et al., *The Journal of Physical Chemistry*, 64(5): 519-524 (1960). This hydrophobic material can be inorganic, organic, or a combination thereof.

The terms "comprises" and variations thereof do not have a limiting meaning where these terms appear in the description and claims.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure.

As used herein, "a," "an," "the," "at least one," and "one or more" are used interchangeably.

As used herein, the term "or" is generally employed in its usual sense including "and/or" unless the content clearly dictates otherwise. The term "and/or" means one or all of the listed elements or a combination of any two or more of the listed elements (e.g., preventing and/or treating an affliction means preventing, treating, or both treating and preventing further afflictions).

All numbers are herein assumed to be modified by the term "about" and preferably with the term "exactly." As used herein in connection with a measured quantity, the term "about" refers to that variation in the measured quantity as would be expected by the skilled artisan making the measurement and exercising a level of care commensurate with the objective of the measurement and the precision of the measuring equipment used. The recitation of numerical ranges by endpoints includes all numbers subsumed within that range (e.g., 1 to 5 includes 1, 1.5, 2, 2.75, 3, 3.80, 4, and 5). All parts recited herein, including those in the Example section below, are by weight unless otherwise indicated.

The above summary of the present disclosure is not intended to describe each disclosed embodiment or every implementation of the present disclosure. The description that follows more particularly exemplifies illustrative embodiments. In several places throughout the application, guidance is provided through lists of examples, which examples can be used in various combinations. In each

BRIEF DESCRIPTION OF THE FIGURES

FIG. 3 is an exploded view of an alternative embodiment of the sterilization indicator of the disclosure.

FIG. 4 is cross-sectional view of the device shown in FIG. 3.

FIG. 5 is an exploded view of a preferred embodiment of a sterilization indicator of the disclosure.

FIG. 6 is a cross-sectional view of the device shown in FIG. 5.

DETAILED DESCRIPTION EXEMPLARY EMBODIMENTS

Figures 1, 2:
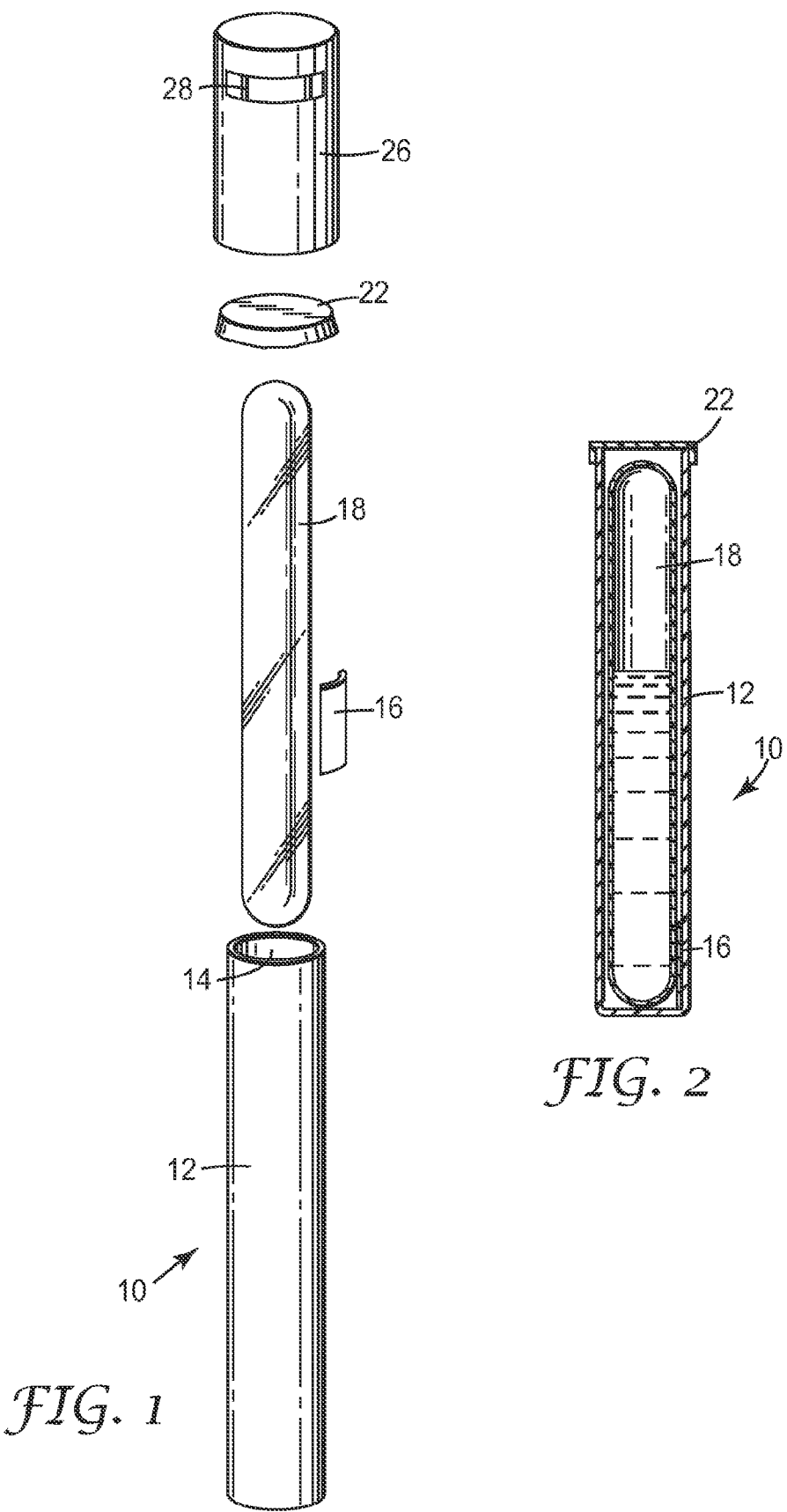
FIG. 1 is an exploded view of an embodiment of a sterilization indicator of the disclosure.
FIG. 2 is a cross-sectional view of the device shown in FIG. 1.

Sterilization indicators for testing the effectiveness of a sterilization procedure are provided, wherein the sterilization indicators include one or more neutralizers.

Generally, herein, a sterilization indicator for testing the effectiveness of a sterilization procedure includes: a container (e.g., a tube, sleeve, or ampoule) having at least one opening to allow a sterilant to enter the container during the sterilization procedure; a carrier contained within the container; biological material supported by the carrier, the biological material being correlated with the survival of at least one test microorganism commonly used to monitor the effectiveness of a sterilization procedure; and means for forming a detectable indication of the failure of a sterilization procedure. Examples of sterilization indicators in which a neutralizer of the present disclosure can be used include that described in U.S. Pat. No. 5,486,459 (Burnham et al.) or U.S. Pat. No. 6,897,059 (Foltz et al.).

The sterilization indicators of the present disclosure can measure spore growth only, enzyme activity only, or both enzyme activity and spore growth following exposure to a sterilization procedure. Preferred sterilization indicators measure the activity of an active enzyme whose activity is correlated with the survival of a test microorganism.

The biological material supported by the carrier is selected such that it is inactivated (e.g., killed) by a sterilization procedure that is lethal to the test microorganism, but wherein the biological material is not inactivated by a sterilization procedure that is sublethal to the test microorganism. That is, the biological material is inactivated as a result of an effective sterilization procedure, and provides a detectable indication as a result of an ineffective sterilization procedure. Preferably, for enzyme-based sterilization indicators, the biological material is a source of an active enzyme, the enzyme having an enzyme activity that is correlated with the survival of at least one test microorganism commonly used to monitor the effectiveness of a sterilization procedure, wherein the source of an active enzyme is inactivated by a sterilization procedure that is lethal to the test microorganism, but wherein the source of an active enzyme is not inactivated by a sterilization procedure that is sublethal to the test microorganism.

Biological material useful in spore outgrowth indicators includes bacteria or fungi in either the spore or vegetative state. For enzyme-based sterilization indicators, the biological material includes a source of active enzyme that may be: (1) the purified, isolated enzyme derived from an appropriate microorganism; (2) a microorganism to which the enzyme is indigenous or added by genetic engineering; or (3) a microorganism to which the enzyme has been added during sporulation or growth. In sterilization indicators of the present disclosure, the biological material (whether it be an enzyme, a microorganism, or spores) is selected such that it is inactivated by a sterilization procedure that is lethal to the test microorganism, but wherein the biological material may not be inactivated by a sterilization procedure that is sublethal to the test microorganism.

The carrier for the biological material can be made of a material that is hydrophobic or hydrophilic. Such materials can be inorganic, organic, or combinations thereof. Carriers that include (or are prepared from) hydrophobic materials can be used with any indicator, whereas carriers that include (or are prepared from) hydrophilic materials are preferably used to monitor a sterilization procedure that uses hydrogen peroxide vapor phase. Examples of suitable hydrophobic materials include polypropylene, polyurethane, nylon, polymer blends containing one or more of these polymers (e.g., with other hydrophobic polymers), or combinations thereof. Examples of suitable hydrophilic materials include glass, rayon, cellulose, polymer blends containing one or more of these polymers (e.g., with other hydrophilic polymers), or combinations thereof.

Sterilization indicators of the disclosure may suitably be used to monitor the effectiveness of one or more types of sterilization procedures, including sterilization procedures that use steam, hydrogen peroxide vapor phase (which may or may not include hydrogen peroxide plasma), ethylene oxide gas, dry heat, propylene oxide gas, methyl bromide, chlorine dioxide, formaldehyde and peracetic acid (alone or with a vapor phase of another material), ozone, and combinations thereof. For example, the sterilization indicators of the disclosure may be used to monitor the effectiveness of any of the hydrogen peroxide plasma sterilization procedures known in the art, including, for example, the procedures described in U.S. Pat. No. 4,643,876 (Jacobs et al.) and U.S. Pat. No. 4,756,882 (Jacobs et al.). Preferably, the sterilization indicator may be used to monitor the effectiveness of a vapor phase sterilization procedure that uses an oxidizing sterilant. More preferably, the sterilization indicator may be used to monitor the effectiveness of a hydrogen peroxide vapor phase sterilization procedure.

While aqueous hydrogen peroxide ($H_2O_2$) has a long history of use as a sterilant, the concept of vapor-phase hydrogen peroxide (VPHP) sterilization has been developed within the past decade. This process is a low temperature sterilization process that kills a wide range of microorganisms including bacterial endospore-forming bacteria commonly used as challenge organisms to evaluate and validate the effectiveness of sterilization cycles in hospitals. A major advantage of hydrogen peroxide is its short exposure cycle time (few minutes). Furthermore, at the end of a hydrogen peroxide sterilization process, only air and water remain in the chamber. Despite these advantages, self-contained rapid-readout biological indicators for hydrogen peroxide sterilization process monitoring are currently unavailable in the marketplace. Significantly, the novel features of the sterilization indicators described herein allow for the development of a rapid-readout hydrogen peroxide sterilization indicator.

In certain situations, one or more components of a sterilization indicator (e.g., carrier of biological material, walls of container) may retain residual oxidizing sterilant. This can occur with hydrogen peroxide vapor as well as with other vapor sterilants such as ozone and peracetic acid. For example, certain carrier materials, particularly those that have a contact angle of zero (i.e., are hydrophilic such as glass fiber and cellulosic materials) can retain residual oxidizing sterilant, particularly hydrogen peroxide. In this context, "residual" means an amount of retained sterilant that inhibits the growth of low numbers of spore survivors. Typically, this means more than 10 micrograms sterilant retained per microgram of carrier. In certain situations, the amount of residual sterilant can be greater than 40 micrograms sterilant per milliliter of growth media. As a comparison, if the carrier material has a contact angle of greater than 90°, it is hydrophobic, and there is generally no more than 10 micrograms sterilant retained per microgram of carrier.

In such sterilization indicators, one or more neutralizers, which is not an enzyme and not a metal catalyst (as defined in U.S. Pat. No. 5,552,320 (Smith)), is disposed within the sterilization indicator. A neutralizer is one that reacts with residual sterilant, e.g., hydrogen peroxide, to neutralize its effect, wherein the neutralizer is not an enzyme, and not a metal catalyst. Enzyme neutralizers are typically not stable at the high temperatures, and thus not desirable.

Suitable examples of neutralizers include sulfur containing materials such as methionine, L-cysteine, D-ethionine, S-methyl-L-cysteine, S-benzyl-L-cysteine, sodium thiosulfate, glutathionine, L-cystathionine, N-acetyl-L-cysteine, carboxymethylcysteine, D,L-homocysteine, D,L-homocysteine-thiolactone, and thiodipropionic acid, and non-sulfur containing materials such as isoascorbic acid, potassium ferricyanide, and sodium pyruvate. Various combinations of such neutralizers can be used. Preferred neutralizers include methionine, L-cysteine, D-ethionine, S-methyl-L-cysteine, S-benzyl-L-cysteine, sodium thiosulfate, thiodipropionic acid, isoascorbic acid, potassium ferricyanide, sodium pyruvate, and combinations thereof.

One or more such neutralizers can be placed in a variety of locations in the sterilization indicator as long as the neutralizer is protected from direct action of the sterilent during the sterilization stage of the process. For example, one or more neutralizers can be located in an eyedropper (as shown in U.S. Pat. No. 5,486,459 (Burnham et al.)), or in an inner container (e.g., ampoule) (as shown in U.S. Pat. No. 6,897,059 (Foltz et al.)) and herein. Preferably, the one or more neutralizers is isolated from the sterilant during the sterilization stage of the process, but then is allowed to come into contact with any residual sterilant during the developing stage of the process (i.e., during the formation of a detectable indication). Preferably, one or more neutralizers is isolated from the sterilization process by locating it in an inner container (e.g., ampoule).

In certain embodiments, the present disclosure provides a sterilization indicator for testing the effectiveness of a sterilization procedure, the indicator including: a container having at least one opening to allow an oxidizing sterilant to enter the outer container during the sterilization procedure; a carrier contained within the container; biological material supported by the carrier, the biological material being correlated with the survival of at least one test microorganism commonly used to monitor the effectiveness of a sterilization procedure, wherein the biological material is inactivated by a sterilization procedure that is lethal to the test microorganism, but wherein the biological material is not inactivated by a sterilization procedure that is sublethal to the test microorganism; wherein one or more components of the sterilization indicator retains residual oxidizing sterilant; a neutralizer disposed within the indicator in an amount effective to neutralize residual oxidizing sterilant, wherein the neutralizer is not an enzyme and not a metal catalyst; and means for forming a detectable indication of the failure of a sterilization procedure. In certain embodiments, the biological material is distributed within (preferably, homogeneously throughout the entire volume of) the carrier.

In sterilization indicators of the present disclosure, the carrier can include a material in a sheet form, whether it is porous or nonporous (preferably, it is porous). Alternatively, it can be in the form of a unique three-dimensional porous configuration that allows for the source of active enzyme to be distributed within a three-dimensional porous carrier. In this context, "distributed within" a three-dimensional porous carrier means that the biological material (e.g., source of active enzyme) may be uniformly or nonuniformly distributed throughout at least a portion of the volume of a three-dimensional porous carrier (as opposed to only on its surface). The biological material is preferably distributed (more preferably, uniformly distributed) throughout the entire volume of a three-dimensional porous carrier, for better results. This can be accomplished by blending (e.g., in a laboratory blender) a sheet material, for example, to form a three-dimensional porous configuration and combining the biological material (e.g., source of active enzyme) before, during, or after blending.

The three-dimensional porous carrier described herein is significantly more voluminous than conventional carriers used in sterilization indicators. By this it is meant, that the carrier material of this embodiment occupies a larger three-dimensional space than conventional carriers, and, hence, is referred to herein as a three-dimensional porous carrier. By comparison, the flat carrier strip disclosed in U.S. Pat. No. 6,897,059 (Foltz et al.) is considered a two-dimensional carrier, and is suitable for certain embodiments of the present disclosure. Typically, a three-dimensional porous carrier occupies at least 5% of the volume of a container in which it is located (e.g., the outer container of a two-container device). In certain embodiments, a three-dimensional porous carrier occupies at least 10%, or at least 15%, or at least 20% of the volume a container in which it is located (e.g., the outer container of a two-container device). Typically, a three-dimensional porous occupies no more than 50%, or no more than 40%, or no more than 30%, of the volume of a container in which it is located (e.g., the outer container of a two-container device).

Typically, the same amount of biological material is distributed within the three-dimensional porous carrier of the present disclosure, when compared to the amount of biological material disposed on conventional two-dimensional and/or nonporous carriers. This can result in a more even distribution of the biological material (e.g., spores), thereby allowing the sterilant to penetrate into the three-dimensional porous carrier more thoroughly and have more uniform contact with the biological material, compared to more densely packed and clustered biological material on conventional carriers. Accordingly, a three-dimensional porous carrier as described herein can provide one or more of the following advantages: faster inactivation (e.g., kill); greater reproducibility; greater accuracy; and a sharper endpoint. In less porous and less voluminous conventional carriers, the biological material can form clumps, which can prohibit the sterilant from penetrating into the center of the clump. As a result, there may not be a sharp endpoint, which can lead to a false indication of sterilization failure. Thus, the physical form of the material (e.g., a voluminous three-dimensional configuration) used as a porous carrier has the ability to enhance the speed and accuracy of a vapor phase sterilization process. This is particularly useful in a hydrogen peroxide vapor process.

In certain embodiments, a three-dimensional porous carrier has a solidity (as defined in the Examples Section) of greater than 5%, greater than 10%, greater than 15%, greater than 20%, greater than 25%, greater than 30%, or greater than 35%. In certain embodiments, a three-dimensional porous carrier has a solidity of no greater than 50%, no greater than 45%, or no greater than 40%.

In certain embodiments, an effective fiber diameter (as defined in the Examples Section) of the material of a three-dimensional porous carrier is greater than 10 microns, greater than 15 microns, greater than 20, greater than 25 microns, greater than 30 microns, greater than 35 microns, greater than 40 microns, greater than 45 microns, or greater than 50 microns. In certain embodiments, an effective fiber diameter of the material of a three-dimensional porous carrier is no greater than 100 microns, no greater than 90 microns, or no greater than 80 microns.

Figure 9B:
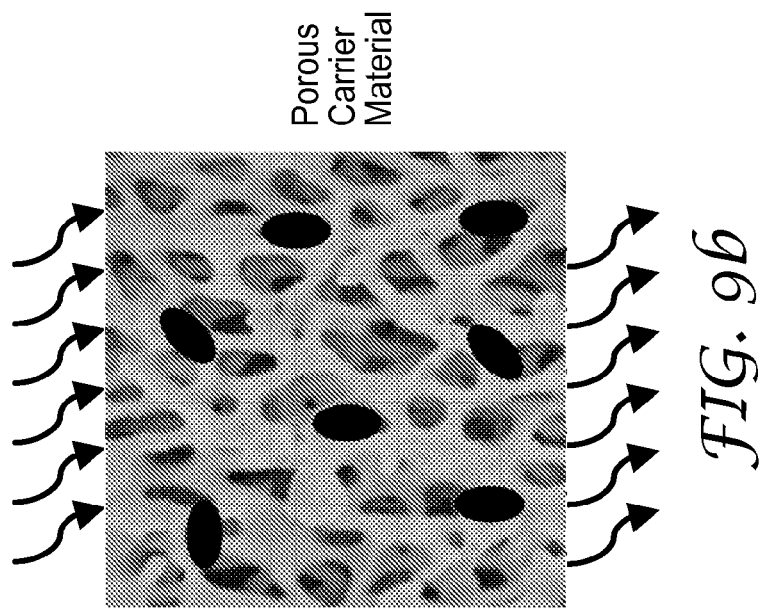
FIG. 9b is an exploded view of the three-dimensional porous carrier with spores distributed within the three-dimensional porous carrier.

A porous carrier can be prepared in a variety of ways. In one exemplary method, as described in greater detail in the Examples Section and illustrated in FIG. 9a, a nonwoven sheet material is converted to a three-dimensional structure (in step 1) by blending it in a laboratory blender to obtain a more voluminous structure (e.g., a three-dimensional structure, similar to that of a cotton ball). Alternatively, it can be chopped, melt-blown, or prepared using standard techniques for preparing nonwoven materials. This three-dimensional porous carrier is then removed from the blender (step 2) and placed into a container (step 3) (e.g., the outer container shown in FIGS. 1 and 2), and the desired biological material (e.g., spores) applied to the porous carrier (step 4). The containers can then be subjected to mixing (e.g., by merely squeezing) and further processing (step 5) as desired depending on the biological material (e.g., incubated for 16 hours (overnight) at 58° C.) to provide biological material distributed within a three-dimensional porous carrier (as shown in FIG. 9b with the arrows represented the flow of sterilant). A sterilization indicator can then be assembled (step 6) by using components such as a barrier, internal ampoule containing enzyme substrate or biological media, for example, a filter, and perforated cap, as is well known to those skilled in the art.

Thus, a sterilization indicator that includes a three-dimensional porous carrier can be prepared by a method that includes: providing a container having at least one opening to allow a sterilant to enter the container during the sterilization procedure; providing a three-dimensional porous carrier (e.g., providing a nonwoven material in the form of a sheet and blending the sheet to form a three-dimensional structure); placing the three-dimensional porous carrier into the container in an amount sufficient to occupy at least 5% of the volume of the container; placing biological material in the three-dimensional porous carrier such that it is distributed within the three-dimensional porous carrier, the biological material being correlated with the survival of at least one test microorganism commonly used to monitor the effectiveness of a sterilization procedure, wherein the biological material is inactivated as a result of an effective sterilization procedure, and provides a detectable indication as a result of an ineffective sterilization procedure; optionally placing means for (i.e., one or more components for) forming a detectable indication of the failure of a sterilization procedure in the container; and assembling the container, three-dimensional porous carrier, biological material, and other optional components (components for forming a detectable indication, barrier, etc.) in an arrangement that forms a sterilization indicator (including other steps that complete the formation of a sterilization indicator such as using a perforated cap, for example).

Sterilization indicators of the present disclosure include a means for forming a detectable indication of the failure of a sterilization procedure. For example, sterilization indicators of the present disclosure can include a means for forming an enzyme-modified product (e.g., formed from reaction of enzyme substrate with active enzyme) that provides a detectable indication of the failure of a sterilization procedure. This is typically referred to as the enzymatic activity test. This detectable indication of the failure of a sterilization procedure preferably includes a detectable fluorescence, luminescence, and/or chromogenic indication. These indications are preferably used for a quick enzymatic response in a rapid-readout sterilization indicator. In this context, "rapid-readout" means that a detectable signal is developed in less than 24 hours, and preferably within 8 hours or less.

In certain embodiments of sterilization indicators of the present disclosure (e.g., dual read-out sterilization indicators and biological indicators based solely on spore growth), the detectable indication of the failure of a sterilization procedure includes a detectable pH indication. The use of pH indication occurs upon growth of spores typically after 24 hours, and often after 7 days. In dual read-out sterilization indicators, this provides a mechanism for verifying the reliability of the rapid-readout. Generally, the pH indicator is one suitable for identification of acid formation, such as bromocresol purple. This provides evidence of the stability and/or reliability of the readout obtained from the fluorescence, luminescence, and/or chromogenic indication, which are used for a quick enzymatic response. This is referred to as the spore outgrowth test.

In such embodiments in which spore outgrowth is evaluated (e.g., in a spore outgrowth indicator), after the sterilization procedure, the spores are brought into contact with growth medium (e.g., soybean casein digest optionally with a pH indicator). For example, an inner container containing growth medium is crushed by compressing an outer container, releasing the growth medium and bringing it into contact with the spores supported by a carrier in an outer container. The indicator is then incubated under conditions that stimulate spore growth. If the sterilization procedure is ineffective, surviving spores will grow out and cause a pH indicator in the growth medium to change color (e.g., as a result of acidic by-products formed from growing spores). This indicates that the sterilization cycle failed to kill the test population of microorganisms and may have failed to kill contaminating microorganisms present in the sterilizer load. Although biological indicators that rely on the growth of spores are accurate, they are slow, commonly requiring between 1 and 7 days to provide a final result.

In certain embodiments of a method of making a sterilization indicator discussed above, the step of placing one or more components for forming a detectable indication of the failure of a sterilization procedure in the container includes placing an inner container including a growth medium that stimulates the growth of live spores and a pH indicator.

In certain embodiments of a method of making a sterilization indicator discussed above, the step of placing one or more components for forming a detectable indication of the failure of a sterilization procedure in the container includes placing an inner container including an enzyme substrate that reacts with the active enzyme to form a detectable enzyme-substrate product.

In certain embodiments, a sterilization indicator includes: a container having at least one opening to allow an oxidizing sterilant to enter the container during the sterilization procedure; a carrier (preferably, a porous carrier) contained within the container; biological material supported by the carrier (preferably, distributed within the porous carrier), the biological material being correlated with the survival of at least one test microorganism commonly used to monitor the effectiveness of a sterilization procedure, wherein the biological material is inactivated as a result of an effective sterilization procedure, and provides a detectable indication as a result of an ineffective sterilization procedure; wherein one or more components of the sterilization indicator retains residual oxidizing sterilant; a neutralizer disposed within the indicator in an amount effective to neutralize residual oxidizing sterilant, wherein the neutralizer is not an enzyme and not a metal catalyst; and means for forming a detectable indication of the failure of a sterilization procedure.

In certain embodiments, a sterilization indicator includes: a container having at least one opening to allow an oxidizing sterilant to enter the container during the sterilization procedure; a carrier (preferably, a porous carrier) contained within the container; biological material comprising a source of an active enzyme, wherein the source of active enzyme is supported by the carrier (preferably, distributed within the porous carrier); wherein the active enzyme has an enzyme activity that is correlated with the survival of at least one test microorganism commonly used to monitor the effectiveness of a sterilization procedure; wherein the source of an active enzyme is inactivated by a sterilization procedure that is lethal to the test microorganism, but wherein the source of an active enzyme is not inactivated by a sterilization procedure that is sublethal to the test microorganism; wherein one or more components of the sterilization indicator retains residual oxidizing sterilant; a neutralizer disposed within the indicator in an amount effective to neutralize residual oxidizing sterilant, wherein the neutralizer is not an enzyme and not a metal catalyst; and means for forming an enzyme-modified product that provides a detectable indication of the failure of a sterilization procedure.

In certain embodiments, sterilization indicators also include a breakable inner container (e.g., a tube, sleeve, or ampoule) within the outer container that is impermeable to the sterilant used in the sterilization procedure. For indicators based on spore outgrowth only, this inner container includes a growth medium that stimulates the growth of live spores. After the sterilization procedure, the inner container is adapted so that it may be broken to allow contact between the growth medium and the spores. For enzyme-based indicators, this inner container includes a substrate, wherein the inner container is adapted so that it may be broken to allow the substrate to react with active enzyme to form an enzyme-modified product that provides a detectable indication of the failure of a sterilization procedure. In such embodiments, preferably the outer container is compressible and the inner container is adapted so that it may be broken by compressing the outer container. Alternatively, the outer container may or may not be compressible and the inner container is adapted so that it may be broken by pushing down a cap to compress the inner container against an element (e.g., a sleeve) with prongs such that the inner container breaks upon being pushed into the prongs.

An exemplary sterilization indicator of the disclosure is shown in FIGS. 1 and 2 and FIGS. 5 and 6 (numbers in parentheses refer to these figures). The sterilization indicator 10 (110) includes nesting containers that separate the various components of the system from each other until after the sterilization cycle is complete. The sterilization indicator 10 (110) includes an outer container 12 (112) (shown here in the form of a tube or ampoule, although other types of containers can be used as would be understood by one of skill in the art), a sealed inner container 18 (118) (shown here in the form of a sealed tube or ampoule, although other types of sealed containers can be used as would be understood by one of skill in the art) and a vented cap 26 (126). Outer container 12 (112) is preferably made of a compressible plastic. Inner container 18 (118) is made of glass or some other frangible material. Closure member 22 (122) is preferably a bacteria impermeable, gas transmissive barrier that fits over the open end 14 (114) of outer container 12 (112). Carrier 16 (116) includes (i.e., supports) biological material (e.g., a source of active enzyme), and is disposed between the inner container 18 (118) and the outer container 12 (112). Inner container 18 (118) contains a neutralizer. In FIGS. 1 and 2 the carrier 16 is a strip of material (e.g., the flat carrier strip, made for example, of paper, as disclosed in U.S. Pat. No. 6,897,059 (Foltz et al.). In FIGS. 5 and 6, the carrier (116) is porous and occupies at least 5% of the volume of the outer container (112). In these embodiments, inner container 18 (118), includes one or more neutralizers as described herein. For an enzyme-based sterilization indicator, inner container 18 (118) also includes an enzyme substrate that reacts with active enzyme that is supported by carrier 16 (116) and creates a detectable signal if the sterilization procedure is ineffective. For a spore outgrowth indicator, inner container 18 (118) also includes a growth medium for any spores that are supported by carrier 16 (116) that survive, wherein spore outgrowth creates a detectable signal if the sterilization procedure is ineffective.

Figures 7, 8:
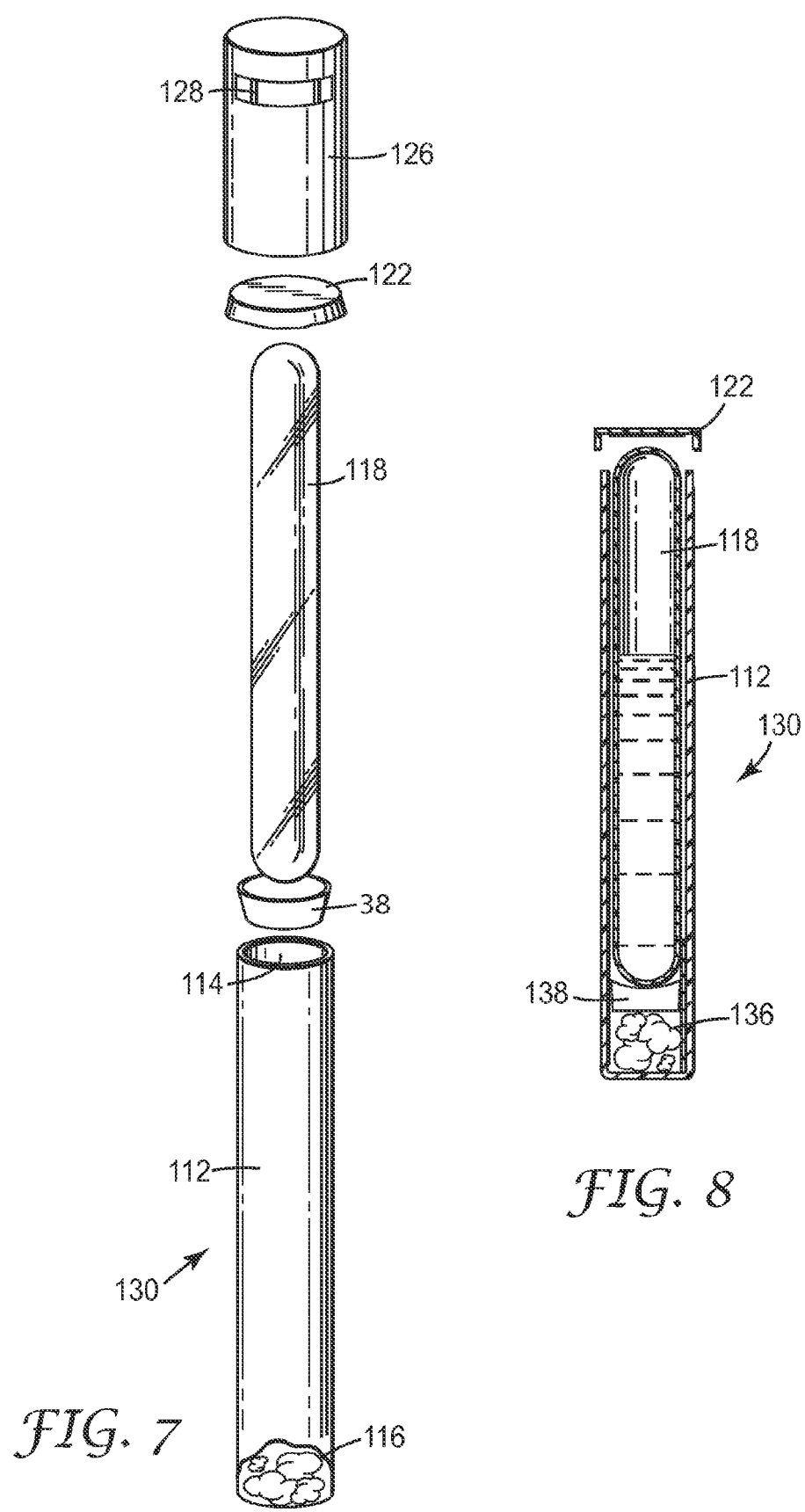
FIG. 7 is an exploded view of an alternative preferred embodiment of the sterilization indicator of the disclosure.
FIG. 8 is cross-sectional view of the device shown in FIG. 7.

FIGS. 3 and 4 and FIGS. 7 and 8 (numbers in parentheses refer to these figures) show an alternative embodiment, in which sterilization indicator 30 (130) includes carrier 36 (136) located within outer container 12 (112) near the closed end of the container, and a barrier 38 (138) is situated between the porous carrier 36 (136) and the inner container 18 (118). In FIGS. 3 and 4 the carrier 36 is a strip of material (e.g., the carrier strip disclosed in U.S. Pat. No. 6,897,059 (Foltz et al.). In FIGS. 7 and 8, carrier (116) is porous and occupies at least 5% of the volume of the outer container (112), and is referred to herein as a three-dimensional porous carrier. In these embodiments, inner container 18 (118), includes one or more neutralizers as described herein. As described in the embodiments of FIGS. 1 and 2 and 5 and 6, for an enzyme-based sterilization indicator, inner container 18 (118) also includes an enzyme substrate that reacts with active enzyme that is supported by carrier 36 (136) and creates a detectable signal if the sterilization procedure is ineffective. For a spore outgrowth indicator, inner container 18 (118) also includes a growth medium for any spores that are supported by carrier 36 (136) that survive, wherein spore outgrowth creates a detectable signal if the sterilization procedure is ineffective.

Alternatively, in certain embodiments, a porous carrier as described herein can be used advantageously without a barrier. For example, a porous carrier that includes a hydrophobic material can function as both a carrier and a barrier.

Barrier 38 (138) serves to isolate the porous carrier 36 (136) from the inner container 18 (118). Barrier 38 (138) is preferably made from a hydrophobic material so that enzyme-modified product, for example, concentrates around the porous carrier and does not diffuse rapidly into the area of the container which is on the other side of the barrier. Maintaining a higher concentration of the enzyme-modified product in the lower portion of the indicator enables the enzyme-modified product, whether it be luminescent or colored, for example, to be detected after a shorter period of incubation than would be the case if the porous carrier 36 (136) was reacted with the entire contents of inner container 18 (118). Preferred devices which incorporate a barrier 38 (138) provide reliable information on sterilization efficacy within about 10 minutes.

The configuration shown in FIGS. 3 and 4 with a barrier 38 is often used in a hydrogen peroxide vapor sterilization procedure. The barrier is preferably a disc of polypropylene blown microfiber material having a weight of 200 g/sq. meter, commercially available as "THINSULATE 200-B brand Thermal Insulation" from 3M Company, St. Paul, Minn. Again, however, if the porous carrier is a hydrophobic material as described herein, the barrier is not needed, even in a hydrogen peroxide sterilization procedure. Also, when the indicator is to be used to monitor hydrogen peroxide procedures (whether using the embodiment shown in FIGS. 1 and 2 or FIGS. 3 and 4), closure member 22 is preferably made of a high-density fiber material, such as TYVEK high-density polyethylene fiber material, commercially available from E.I. du Pont de NeMours and Co., Wilmington, Del.

Referring to FIGS. 1 and 2 and FIGS. 5 and 6 (numbers in parentheses refer to these figures), during a typical sterilization procedure sterilant enters the outer container 12 (112) through the vents 28 (128) on cap 26 (126) and contacts the biological material (e.g., source of active enzyme) supported by carrier 16 (116) but does not contact the contents in the sealed inner container 18 (118) (e.g., substrate solution and/or growth medium). After the sterilization cycle the sides of the outer container 12 (112) are compressed, breaking the inner container 18 (118) and bringing the contents of the inner container 18 (118) and the biological material supported by carrier 16 (116) into contact with each other. The sterilization indicator is then incubated for a period of time sufficient for any remaining biological material (e.g., active enzyme or live spores) to form a detectable indication. For example, if the biological material is active enzyme, incubation occurs for a sufficient time for it to react with the substrate to form an enzyme-modified product that produces a detectable signal, such as luminescence, fluorescence or a color change, indicating that the sterilization procedure may have been ineffective In a preferred embodiment of the sterilization indicator 10 (110) of the disclosure, the biological material supported by carrier 16 (116) is a source of an active enzyme. Preferably, the source of an active enzyme is a live microorganism, such as a bacterial or fungal spore. In the most preferred embodiment, spores are the source of active enzyme, and the sterilization indicator 10 (110) is a dual rapid-readout indicator that monitors the effectiveness of a sterilization procedure by measuring both enzyme activity and spore outgrowth. In this embodiment, the inner container 18 (118) contains spore growth medium and enzyme substrate. After the sterilization cycle is complete, the inner container 18 (118) is broken, and the carrier 16 (116) is exposed to its contents and incubated. The enzyme test produces visible results within a few hours, and the live microorganism growth test confirms these results within 7 days.

The theory underlying the operation of enzyme indicators is that the inactivation of the enzyme will be correlated with the death of test microorganisms in the indicator. The enzyme selected for use in a sterilization indicator must be at least as resistant to a sterilization procedure as microorganisms that are likely to be present as contaminants, and preferably more resistant than such microorganisms. The enzyme should remain sufficiently active to form a detectable enzyme-substrate product after a sterilization cycle that fails to kill contaminating microorganisms, yet be inactivated by a sterilization cycle that kills contaminating microorganisms.

As stated above, the source of active enzyme may be: (1) the purified, isolated enzyme derived from an appropriate microorganism; (2) a microorganism to which the enzyme is indigenous or added by genetic engineering; or (3) a microorganism to which the enzyme has been added during sporulation or growth, such that the enzyme is incorporated or associated with the microorganism, e.g., an enzyme added to a spore during sporulation which becomes incorporated within the spore.

Enzymes that are suitable for use in the sterilization indicators of the disclosure are described in U.S. Pat. No. 5,252,484 (Matner et al.) and U.S. Pat. No. 5,073,488 (Matner et al.). Suitable enzymes include enzymes derived from spore-forming microorganisms, such as *Geobacillus stearothermophilus* and *Bacillus atrophaeus* (formerly known as *Bacillus subtilis*). Enzymes from spore-forming microorganisms that are useful in the sterilization indicators of the disclosure include beta-D-glucosidase, alpha-D-glucosidase, alkaline phosphatase, acid phosphatase, butyrate esterase, caprylate esterase lipase, myristate lipase, leucine aminopeptidase, valine aminopeptidase, chymotrypsin, phosphohydrolase, alpha-D-galactosidase, beta-D-galactosidase, tyrosine aminopeptidase, phenylalanine aminopeptidase, beta-D-glucuronidase, alpha-L-arabinofuranosidase, N-acetyl-B-glucosaminodase, beta-D-cellobiosidase, alanine aminopeptidase, proline aminopeptidase and a fatty acid esterase, derived from spore forming microorganisms.

When a microorganism is used as the source of active enzyme, the method of the present disclosure may include the step of incubating any of the microorganisms which remain viable, following the completion of the sterilization cycle, with an aqueous nutrient medium. Inclusion of this step confirms by conventional techniques whether the sterilization conditions had been sufficient to kill all of the microorganisms in the indicator, indicating that the sterilization conditions had been sufficient to sterilize all of the items in the sterilizer. If growth of the microorganism is used in a conventional manner to confirm the results of the enzyme test, the microorganism should be one which is conventionally used to monitor sterilization conditions. These conventionally used microorganisms are generally many times more resistant to the sterilization process being employed than most organisms encountered in natural contamination.

Preferred microorganisms, which may be utilized as the source of active enzyme, or as the biological material useful in spore outgrowth indicators, are bacteria or fungi in either the spore or vegetative state. The bacterial spore is recognized as the most resistant form of microbial life. It is the life form of choice in all tests for determining the sterilizing efficacy of devices, chemicals and processes. Particularly preferred sources of enzyme include *Bacillus, Clostridium, Neurospora,* and *Candida* species of microorganisms. Spores from *Bacillus* and *Clostridia* species are the most commonly used to monitor sterilization processes utilizing saturated steam, dry heat, gamma irradiation, and ethylene oxide.

Particularly preferred microorganisms commonly used to monitor sterilization conditions include *Geobacillus stearothermophilus* and *Bacillus atrophaeus*. *Geobacillus stearothermophilus* is particularly useful to monitor sterilization under steam sterilization conditions. The enzyme alpha-D-glucosidase has been identified in spores of *Geobacillus stearothermophilus*, such as those commercially available as "ATCC 7953" from American Type Culture Collection, Rockville, Md. *Bacillus atrophaeus* is particularly useful to monitor conditions of gas and dry heat sterilization. The enzyme beta-D-glucosidase has been found in *Bacillus atrophaeus* (e.g., commercially available as "ATCC 9372" from American Type Culture Collection).

Where dual rapid-readout indicators are used, these microorganisms may serve as both the source of active enzyme in the rapid enzyme test and the test microorganism for the spore outgrowth test. *Geobacillus stearothermophilus* is particularly preferred for monitoring both steam and hydrogen peroxide plasma sterilization procedures. *Bacillus atrophaeus* is particularly preferred for monitoring ethylene oxide sterilization procedures and may be used to monitor hydrogen peroxide plasma sterilization procedures.

Alternatively, in the event that isolated enzyme is utilized, or the microorganism used as the source of the enzyme is not more resistant to the sterilization conditions than the natural contaminants, another microorganism commonly used to monitor sterilization conditions can be exposed to the sterilization cycle along with the enzyme source. Again, in such a case, the method of the present disclosure may include the step of incubating any viable microorganism remaining after the sterilization cycle with an aqueous nutrient medium to confirm the sterilization efficacy.

The present disclosure, although herein described primarily in terms of a single enzyme and/or microorganism species, should be understood to refer as well to the use is of a plurality of enzymes and/or microorganism species. For example, a single sterility indicator may contain three types of isolated enzymes (which may be derived from three types of microorganisms), one enzyme being resistant to heat, a second being resistant to gaseous sterilizing media, and a third being resistant to radiation, e.g., gamma and beta irradiation. Similarly, a single sterility indicator may contain three species of microorganisms, one species being resistant to heat, a second species being resistant to gaseous sterilizing media, and the third species being resistant to radiation.

Enzyme substrates that are suitable for use in the sterilization indicators of the disclosure are described in U.S. Pat. No. 5,252,484 (Matner et al.) and U.S. Pat. No. 5,073,488 (Matner et al.). Chromogenic and fluorogenic substrates that react with enzymes to form detectable products, and that are suitable for use in the sterilization indicator of the disclosure, are well known in the art. (M. Roth, "*Fluorimetric Assay of Enzymes*"; *Methods of Biochemical Analysis*, Vol. 17, D. Glick, Ed., Interscience Publishers, New York, 1969, pp. 189-192; S. Udenfriend, Chapter 9—*Fluorescence in Enzymology*", *Fluorescence Assay in Biology and Medicine*, Academic Press, New York, 1962, pp. 312-348; D. J. R. Laurence, Fluorescence Techniques for the Enzymologist, *Methods in Enzymology*, Vol. 4, S. P. Colowick and N. O. Kaplan, Eds., Academic Press, New York, 1957, pp. 174-212). These substrates may be classified in two groups based on the manner in which they create a visually detectable signal. The substrates in the first group react with enzymes to form enzyme-modified products that are themselves chromogenic or fluorescent. The substrates in the second group form enzyme-modified products that must react further with an additional compound to generate a color or fluorescent signal.

The present disclosure also provides methods of use. In general, the present disclosure provides a method for testing the effectiveness of a sterilization procedure, the method comprising: providing a sterilization indicator as described herein; subjecting the sterilization indicator comprising biological material to a sterilization procedure; subsequent to sterilization, subjecting the sterilization indicator to a developing procedure to determine whether a detectable indication is present or absent; and correlating the presence of the detectable indication with failure of the sterilization procedure and the absence of the detectable indication with success of the sterilization procedure.

Using an exemplary spore outgrowth sterilization indicator, a method for testing the effectiveness of a sterilization procedure includes: providing a sterilization indicator comprising: a carrier; biological material comprising spores, wherein the spores are supported by the carrier; the biological material being correlated with the survival of at least one test microorganism commonly used to monitor the effectiveness of a sterilization procedure, wherein the biological material is inactivated as a result of an effective sterilization procedure, and provides a detectable indication as a result of an ineffective sterilization procedure; wherein one or more components of the sterilization indicator retains residual oxidizing sterilant; and a neutralizer disposed within the indicator in an amount effective to neutralize residual oxidizing sterilant, wherein the neutralizer is not an enzyme and not a metal catalyst; subjecting the sterilization indicator comprising biological material to a sterilization procedure; subsequent to sterilization, combining the biological material with a growth medium that includes a pH indicator, and incubating the mixture of biological material and growth medium under conditions that stimulate spore growth; determining whether surviving spores, which have a detectable pH signal, are present or absent in the biological material; and correlating the presence of the detectable signal with failure of the sterilization procedure and the absence of the detectable signal with success of the sterilization procedure.

Using an exemplary enzyme-based sterilization indicator, a method for testing the effectiveness of a sterilization procedure includes: providing a sterilization indicator comprising: a carrier; biological material comprising a source of an active enzyme, wherein the source of active enzyme is supported by the carrier; wherein the active enzyme has an enzyme activity that is correlated with the survival of at least one test microorganism commonly used to monitor the effectiveness of a sterilization procedure; wherein the source of an active enzyme is inactivated by a sterilization procedure that is lethal to the test microorganism, but wherein the source of an active enzyme is not inactivated by a sterilization procedure that is sublethal to the test microorganism; wherein one or more components of the sterilization indicator retains residual oxidizing sterilant; a neutralizer disposed within the indicator in an amount effective to neutralize residual oxidizing sterilant, wherein the neutralizer is not an enzyme and not a metal catalyst; and an enzyme substrate that reacts with the active enzyme to form an enzyme-modified product, which has a detectable signal, upon failure of a sterilization procedure; subjecting the source of active enzyme to a sterilization procedure; combining the enzyme and the substrate to form an enzyme-modified product; determining whether the enzyme-modified product, which has a detectable signal, is present or absent; and correlating the presence of the detectable signal with failure of the sterilization procedure and the absence of the detectable signal with success of the sterilization procedure.

In a particularly preferred embodiment, the sterilization indicator is a dual rapid-readout indicator and the source of active enzyme comprises spores of a microorganism that serve as both the source of active enzyme for the enzyme activity test, and the test microorganism for the spore outgrowth test. Suitable microorganisms include *Geobacillus stearothermophilus* and *Bacillus atrophaeus*. In the most preferred embodiment, *Geobacillus stearothermophilus* spores are used in the indicators.

Referring to FIGS. 1 and 2, in an exemplary use wherein the biological material includes spores, the sterilization indicator 10 is placed in the sterilization chamber and exposed to a hydrogen peroxide vapor sterilization procedure. Sterilant enters the indicator 10 through vent 28 and closure member 22, and contacts the spores supported by the carrier 16. After the procedure is completed, the indicator 10 is removed from the sterilization chamber and the sides of the outer container 12 are compressed, breaking the frangible inner container 18 and releasing the growth medium that includes a pH indicator so that it may contact the spores supported by carrier 16. The sterilization indicator 10 is then incubated for a period of time sufficient for any surviving spores remaining in the indicator to grow and cause a color change in the pH indicator, which provides a detectable indication of the failure of the sterilization procedure. If the sterilization procedure is effective and all spores have been inactivated, then no color change is generated upon incubation.

Referring to FIGS. 1 and 2, in an exemplary use wherein the biological material includes a source of an active enzyme, the sterilization indicator 10 is placed in the sterilization chamber and exposed to a hydrogen peroxide vapor sterilization procedure. Sterilant enters the indicator 10 through vent 28 and closure member 22, and contacts the source of active enzyme supported by the carrier 16. After the procedure is completed, the indicator 10 is removed from the sterilization chamber and the sides of the outer container 12 are compressed, breaking the frangible inner container 18 and releasing the enzyme substrate so that it may contact the source of active enzyme supported by carrier 16. The sterilization indicator 10 is then incubated for a period of time sufficient for any active enzyme remaining in the indicator to react with the substrate and form an enzyme-modified product, which provides a detectable indication of the failure of the sterilization procedure. The enzyme-modified product may be detectable as fluorescence, luminescence or a color change. If the sterilization procedure is effective and all active enzyme has been inactivated, then no detectable signal is generated upon incubation.

Figure 10:
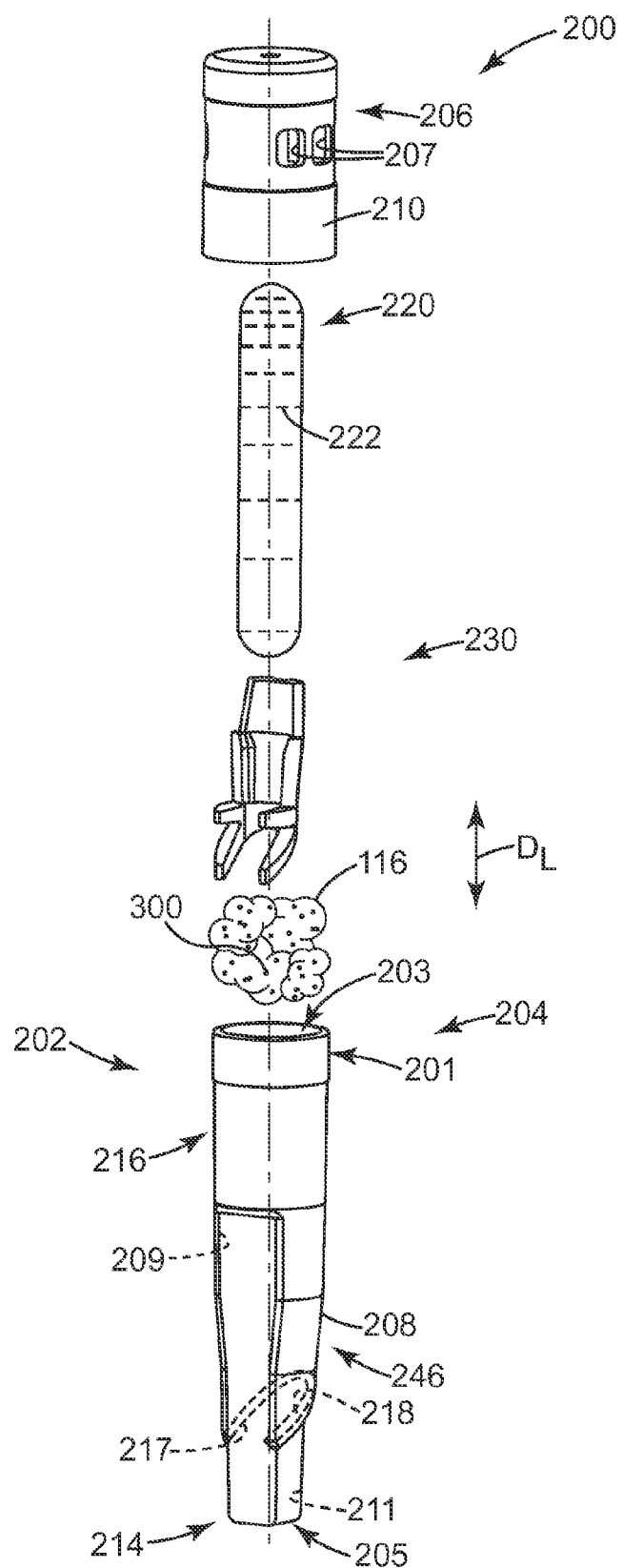
FIG. 10 is an exploded view of an alternative preferred embodiment of the sterilization indicator of the disclosure.
Figure 11:
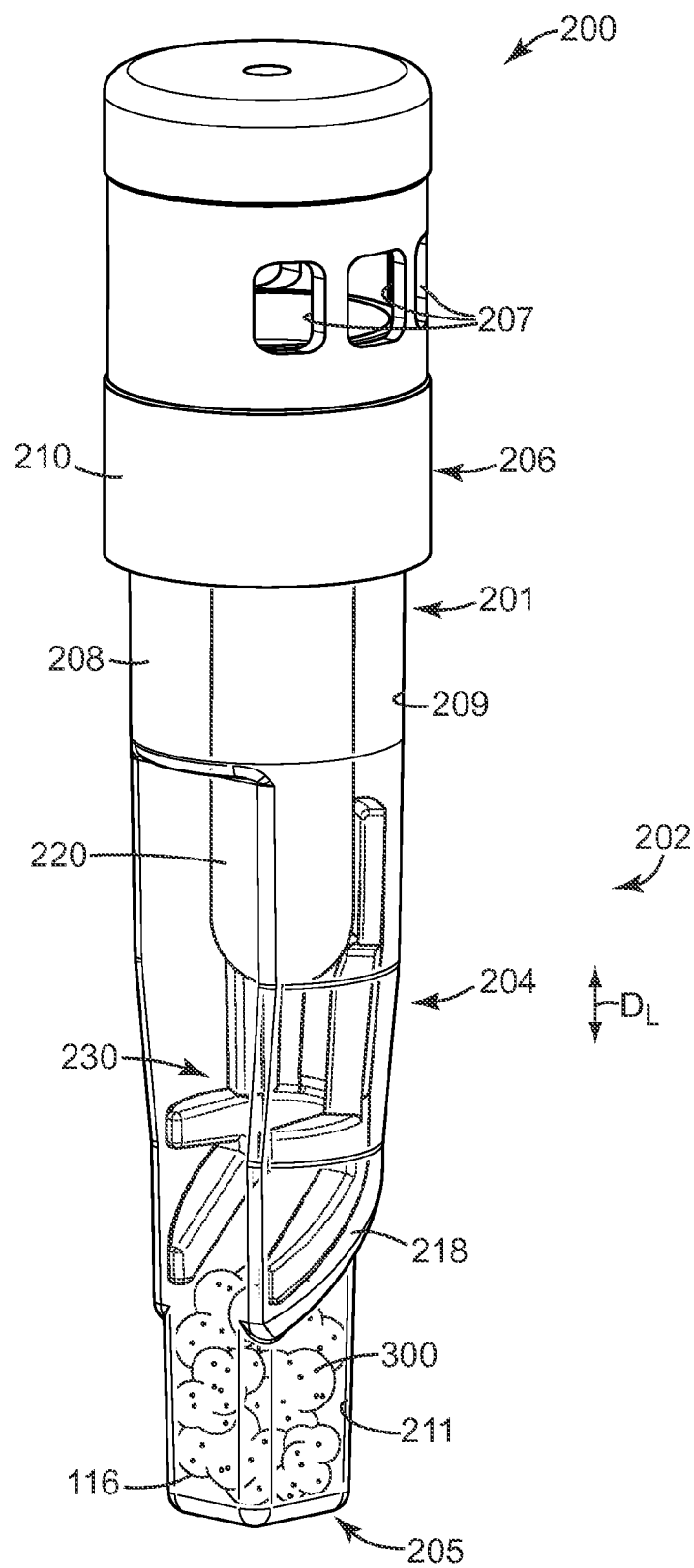
FIG. 11 is a perspective view of the device shown in FIG. 10.

Another exemplary sterilization indicator of the present disclosure is shown in FIGS. 10-11. The biological sterilization indicator 200 includes a housing 202, which contains a first portion 204 (e.g., a hollow tube) and a second portion 206 (e.g., a cap) that are coupled together to provide a self-contained biological sterilization indicator. The cap may be a molded polypropylene with general dimensions of approximately 21 mm long by 14 mm in diameter. The first portion 204 (hollow tube) may be a molded polycarbonate, with the general dimensions of about 52 mm long and 12 mm in diameter at top, with the shape shown in FIGS. 10-11. The total volume of the first portion 204 (e.g., a hollow tube) is approximately 3 mL.

The housing 202 can be defined by at least one liquid impermeable wall, such as a wall 208 of the first portion 204 and/or a wall 210 of the second portion 206. It should be understood that a one-part unitary housing 202 may also be employed or that the first and second portions 204 and 206 can take on other shapes, dimensions, or relative structures without departing from the spirit and scope of the present disclosure. Suitable materials for the housing 202 (e.g., the walls 208 and 210) can include, but are not limited to, a glass, a metal (e.g., foil), a polymer (e.g., polycarbonate (PC), polypropylene (PP), polyphenylene (PPE), polythyene, polystyrene (PS), polyester (e.g., polyethylene terephthalate (PET)), polymethyl methacrylate (PMMA or acrylic), acrylonitrile butadiene styrene (ABS), cyclo olefin polymer (COP), cyclo olefin copolymer (COC), polysulfone (PSU), polyethersulfone (PES), polyetherimide (PEI), polybutyleneterephthalate (PBT)), a ceramic, a porcelain, or combinations thereof.

The second portion (cap) 206 of the housing 202 may include 6 apertures or openings 207, which provide fluid communication between the interior of the housing 202 (e.g., the reservoir 203) and ambience. A filter paper material (not shown) which acts as a barrier; is positioned in the sterilant path over the apertures 207 and held in place with a pressure sensitive adhesive backed paper label. The filter paper material is the same material present in the cap of currently available 3M ATTEST 1291 Rapid Readout Biological Indicators for Steam Sterilizers (available from 3M Company, St. Paul, Minn.).

The biological sterilization indicator 200 further includes a frangible container 220 that contains a liquid growth media 222. The frangible container 220 is made of borosilicate glass and contains the spore growth media. The media consists of a modified Tryptic Soy Broth (TSB) containing a pH indicator bromocresol purple, and a fluorescent enzyme substrate 4-Methylumbelliferyl-alpha-D-glucoside. The ampoule was approximately 40 mm long by about 4 mm in diameter and held approximately 500 µL of media liquid. An example of a suitable liquid growth media 222 is the media used in product currently available from 3M Company as 3M ATTEST 1292 Rapid Readout Biological Indicators for Steam Sterilizers.

The liquid media container 220 may be held in place within the biological sterilization indicator 200 by an insert 230. The insert (also called a breaker) 230 serves to both hold the container 220 in place and function to facilitate the controlled breakage of the container 220. Controlled breakage occurs during the activation step of the BI, when the second portion (cap) 206 is pushed down to break the liquid media container 220. The insert 230 may be a molded polycarbonate structure with approximate dimensions of 22 mm long by 9 mm wide.

The second portion 206 has a seal positioned to contact the first end 201 of the first portion 204, at the open upper end of the first portion 204 to close or seal (e.g., hermetically seal) the biological sterilization indicator 200 after activation.

The biological sterilization indicator 200 further includes suitable sterilant-resistant spores such as *G. stearothermophilus* spores (ATCC 7953) 300 positioned in fluid communication with the first portion 204. The spores 300 are deposited on a spore carrier 116.

The housing 202 includes a lower portion 214 (that at least partially defines a first chamber 209) and an upper portion 216 (that at least partially defines a second chamber 211), which are partially separated by an inner partial wall or ledge 218, in which is formed an opening 217 that provides fluid communication between the first chamber 209 and the second chamber 211. The second chamber 211 is adapted to house the spore carrier 116. The first chamber 209 is adapted to house the frangible container 220, particularly before activation. The wall 218 is angled or slanted, at a non-zero and non-right angle with respect to the longitudinal direction $D_L$ of the housing 202.

The second chamber 211, which can also be referred to as the "spore growth chamber" or "detection chamber," includes a volume to be interrogated for spore viability to determine the efficacy of a sterilization process.

The liquid media container 220 is positioned and held in place by insert 230 in the first chamber 209. The spores 300 are positioned on the spore carrier 116 and housed in the second chamber 211 and in fluid communication with ambience during sterilization. The sterilant moves into the second chamber 211 (e.g., via the first chamber 109) during sterilization. After the sterilization cycle the BI is intentionally activated and the liquid media 222 moves into the second chamber 211 (e.g., from the first chamber 209) when the container 220 is fractured and the liquid 222 is released into the interior of the housing 202.

The first chamber 209 has a volume of about 2800 microliters (empty of all internal components). The cross-sectional area of the first chamber 209, immediately above the wall 218 is approximately 50 mm². The second chamber 211 has a volume of about 210 microliters. The cross-sectional area of the second chamber 211, immediately below the wall 218, is approximately 20 mm².

The housing 202 is tapered (see, e.g., the tapered portion 246) so that the cross-sectional area in the housing 202 generally decreased along the longitudinal direction $D_L$ from the first end 201 of first portion 204 to the closed end 205 of the housing 202.

Any of the sterilization indicators of the disclosure may be used as part of a test pack. In one embodiment of the disclosure, non-challenge test pack of the disclosure provides no additional resistance to the sterilization procedure above the resistance of the sterilization indicator alone. The non-challenge test pack provides an advantage over the use of the indicator without a test pack in that it securely holds the sterilization indicator in a single position during the sterilization procedure. The non-challenge test pack thus alleviates a problem that occurs when sterilization indicators, which are typically small and prone to roll about, become displaced or misplaced in a load of materials during a sterilization procedure. An alternative test pack, referred to as a lumen-challenge test pack, which provides additional resistance to a sterilization indicator that is equivalent to the resistance the indicator would experience if placed within a lumen having a defined cross-sectional area and length. Lumen-challenge test packs provide an accurate method of determining whether a sterilization procedure would be effective in killing microorganisms that may be located deep within the interior of a tube-like instrument. Exemplary non-challenge and lumen-challenge sterilization test packs are described in U.S. Pat. No. 6,897,059 (Foltz et al.).

The operation of the present disclosure will be further described with regard to the following detailed embodiments and examples. These embodiments and examples are offered to further illustrate the various specific and preferred embodiments and techniques. It should be understood, however, that many variations and modifications may be made while remaining within the scope of the present disclosure.

Exemplary Embodiments

1. A sterilization indicator for testing the effectiveness of a sterilization procedure, the indicator comprising:
a container having at least one opening to allow an oxidizing sterilant to enter the container during the sterilization procedure;
a carrier contained within the container;
biological material supported by the carrier, the biological material being correlated with the survival of at least one test microorganism commonly used to monitor the effectiveness of a sterilization procedure, wherein the biological material is inactivated as a result of an effective sterilization procedure, and provides a detectable indication as a result of an ineffective sterilization procedure;
wherein one or more components of the sterilization indicator retains residual oxidizing sterilant;
a neutralizer disposed within the indicator in an amount effective to neutralize residual oxidizing sterilant, wherein the neutralizer is not an enzyme and not a metal catalyst; and
means for forming a detectable indication of the failure of a sterilization procedure.

2. A sterilization indicator for testing the effectiveness of a sterilization procedure, the indicator comprising:
a container having at least one opening to allow an oxidizing sterilant to enter the container during the sterilization procedure;
a carrier contained within the container;
biological material comprising a source of an active enzyme, wherein the source of active enzyme is supported by the carrier; wherein the active enzyme has an enzyme activity that is correlated with the survival of at least one test microorganism commonly used to monitor the effectiveness of a sterilization procedure; wherein the source of an active enzyme is inactivated by a sterilization procedure that is lethal to the test microorganism, but wherein the source of an active enzyme is not inactivated by a sterilization procedure that is sublethal to the test microorganism;
wherein one or more components of the sterilization indicator retains residual oxidizing sterilant;
a neutralizer disposed within the indicator in an amount effective to neutralize residual oxidizing sterilant, wherein the neutralizer is not an enzyme and not a metal catalyst; and
means for forming an enzyme-modified product that provides a detectable indication of the failure of a sterilization procedure.

3. A sterilization indicator for testing the effectiveness of a sterilization procedure, the indicator comprising:
an outer container having at least one opening to allow sterilant to enter the outer container during the sterilization procedure;
a carrier contained within the outer container;
biological material comprising a source of an active enzyme, wherein the source of active enzyme is supported by the carrier; wherein the active enzyme has an enzyme activity that is correlated with the survival of at least one test microorganism commonly used to monitor the effectiveness of a sterilization procedure; wherein the source of an active enzyme is inactivated by a sterilization procedure that is lethal to the test microorganism, but wherein the source of an active enzyme is not inactivated by a sterilization procedure that is sublethal to the test microorganism;
wherein one or more components of the sterilization indicator retains residual oxidizing sterilant;
a neutralizer disposed within the indicator in an amount effective to neutralize residual oxidizing sterilant, wherein the neutralizer is not an enzyme and not a metal catalyst; and
a breakable inner container within the outer container, wherein the inner container: is impermeable to the sterilant used in the sterilization procedure; includes an enzyme substrate; and is adapted so that it may be broken to allow the enzyme substrate to react with active enzyme to form an enzyme-modified product that provides a detectable indication of the failure of a sterilization procedure.

4. A rapid-readout hydrogen peroxide sterilization indicator for testing the effectiveness of a hydrogen peroxide sterilization procedure, the indicator comprising:

an outer container having at least one opening to allow hydrogen peroxide sterilant to enter the outer container during the sterilization procedure;

a carrier contained within the outer container;

biological material comprising a source of an active enzyme, wherein the source of active enzyme is supported by the carrier; wherein the active enzyme has an enzyme activity that is correlated with the survival of at least one test microorganism commonly used to monitor the effectiveness of a sterilization procedure; wherein the source of an active enzyme is inactivated by a sterilization procedure that is lethal to the test microorganism, but wherein the source of an active enzyme is not inactivated by a sterilization procedure that is sublethal to the test microorganism;

wherein one or more components of the sterilization indicator retains residual hydrogen peroxide sterilant; and a breakable inner container within the outer container, wherein the inner container:

is impermeable to the hydrogen peroxide sterilant used in the sterilization procedure;

includes a mixture comprising an enzyme substrate and a neutralizer disposed within the indicator in an amount effective to neutralize residual hydrogen peroxide sterilant, wherein the neutralizer is not an enzyme and not a metal catalyst; and is adapted so that it may be broken to allow the enzyme substrate to react with active enzyme to form an enzyme-modified product that provides a detectable indication of the failure of a hydrogen peroxide sterilization procedure, wherein the detectable indication is formed within 8 hours or less.

5. The sterilization indicator of any one of embodiments 1 through 4, wherein the neutralizer is a sulfur-containing compound.

6. The sterilization indicator of embodiment 5, wherein the sulfur-containing compound is selected from the group consisting of methionine, L-cysteine, D-ethionine, S-methyl-L-cysteine, S-benzyl-L-cysteine, sodium thiosulfate, glutathionine, L-cystathionine, N-acetyl-L-cysteine, carboxymethylcysteine, D,L-homocysteine, D,L-homocysteine-thiolactone, thiodipropionic acid, and combinations thereof.

7. The sterilization indicator of any one of embodiments 1 through 4, wherein the neutralizer is a non-sulfur-containing compound.

8. The sterilization indicator of embodiment 7, wherein the non-sulfur-containing compound is selected from the group consisting of isoascorbic acid, potassium ferricyanide, sodium pyruvate, and combinations thereof.

9. The sterilization indicator of any one of embodiments 1 through 8, wherein the neutralizer is isolated from the sterilant during sterilization.

10. The sterilization indicator of any one of embodiments 1 through 9, wherein the carrier comprises a material in a sheet form.

11. The sterilization indicator of any one of embodiments 1 through 10, wherein the carrier comprises a porous carrier and the biological material is distributed within the carrier.

12. The sterilization indicator of embodiment 11, wherein the porous carrier occupies at least 5% of the volume of the container in which it is located.

13. The sterilization indicator of embodiment 11 or 12, wherein biological material is uniformly distributed throughout the entire volume of the carrier.

14. The sterilization indicator of embodiment 12 or 13, wherein the porous carrier occupies no more than 50% of the volume of the container.

15. The sterilization indicator of any one of embodiments 12 through 14, wherein the porous carrier has a solidity of greater than 5%.

16. The sterilization indicator of any one of embodiments 12 through 15, wherein the porous carrier has an effective fiber diameter of greater than 10 microns.

17. The sterilization indicator of any one of embodiments 1 through 16, wherein the carrier retains residual oxidizing sterilant.

18. The sterilization indicator of any one of embodiments 1 through 16, wherein the carrier comprises a hydrophobic material.

19. The sterilization indicator of embodiment 18, wherein the hydrophobic material comprises polypropylene, polyurethane, nylon, polymer blends containing one or more of these polymers, or combinations thereof.

20. The sterilization indicator of any one of embodiments 1 through 16, wherein the carrier comprises a hydrophilic material.

21. The sterilization indicator of embodiment 20, wherein the hydrophilic material comprises glass, rayon, cellulose, polymer blends containing one or more of these polymers, or combinations thereof.

22. The sterilization indicator of any one of embodiments 1 through 21, wherein the detectable indication of the failure of a sterilization procedure comprises a detectable fluorescence, luminescence, and/or chromogenic indication.

23. The sterilization indicator of any one of embodiments 1 through 22, wherein the detectable indication of the failure of a sterilization procedure comprises a detectable pH indication.

24. The sterilization indicator of any one of embodiments 1 through 23, wherein the biological material comprises a microorganism.

25. The sterilization indicator of any one of embodiments 1 through 23, wherein the biological material comprises an isolated enzyme.

26. The sterilization indicator of embodiment 1 and 5 through 21 as they depend on embodiment 1, which is a spore outgrowth indicator, wherein the biological material comprises spores, and the detectable indication comprises a pH indication.

27. The sterilization indicator of embodiment 1 and 5 through 21 as they depend on embodiment 1, which is an enzyme-based indicator, wherein the biological material comprises a source of an active enzyme, and the detectable indication comprises a detectable fluorescence, luminescence, and/or chromogenic indication.

28. The sterilization indicator of embodiment 27, which is a dual enzyme-based/spore outgrowth indicator, wherein the biological material comprises a source of an active enzyme that is also suitable for a spore outgrowth test, and the detectable indication comprises a detectable fluorescence, luminescence, and/or chromogenic indication followed by a pH indication.

29. The sterilization indicator of any one of embodiments 1 through 3, and embodiments 4 through 28 as they depend on any one of embodiments 1 through 3, wherein the oxidizing sterilant comprises hydrogen peroxide vapor.

30. The sterilization indicator of embodiment 29, wherein hydrogen peroxide vapor comprises hydrogen peroxide plasma.

31. A method for testing the effectiveness of a sterilization procedure, the method comprising:
providing a sterilization indicator comprising:
a container having at least one opening to allow an oxidizing sterilant to enter the container during the sterilization procedure;
a carrier contained within the container;
biological material supported by the carrier, the biological material being correlated with the survival of at least one test microorganism commonly used to monitor the effectiveness of a sterilization procedure, wherein the biological material is inactivated as a result of an effective sterilization procedure, and provides a detectable indication as a result of an ineffective sterilization procedure;
wherein one or more components of the sterilization indicator retains residual oxidizing sterilant;
a neutralizer disposed within the indicator in an amount effective to neutralize residual oxidizing sterilant, wherein the neutralizer is not an enzyme and not a metal catalyst; and
means for forming a detectable indication of the failure of a sterilization procedure;
subjecting the sterilization indicator comprising biological material to a sterilization procedure;
subsequent to sterilization, subjecting the sterilization indicator to a developing procedure to determine whether a detectable indication is present or absent; and
correlating the presence of the detectable indication with failure of the sterilization procedure and the absence of the detectable indication with success of the sterilization procedure.

32. A method for testing the effectiveness of a sterilization procedure, the method comprising:
providing a sterilization indicator comprising:
a carrier;
biological material comprising spores, wherein the spores are supported by the carrier; the biological material being correlated with the survival of at least one test microorganism commonly used to monitor the effectiveness of a sterilization procedure, wherein the biological material is inactivated as a result of an effective sterilization procedure, and provides a detectable indication as a result of an ineffective sterilization procedure;
wherein one or more components of the sterilization indicator retains residual oxidizing sterilant; and
a neutralizer disposed within the indicator in an amount effective to neutralize residual oxidizing sterilant, wherein the neutralizer is not an enzyme and not a metal catalyst;
subjecting the sterilization indicator comprising biological material to a sterilization procedure;
subsequent to sterilization, combining the biological material with a growth medium that includes a pH indicator, and incubating the mixture of biological material and growth medium under conditions that stimulate spore growth;
determining whether surviving spores, which have a detectable pH signal, are present or absent in the biological material; and
correlating the presence of the detectable signal with failure of the sterilization procedure and the absence of the detectable signal with success of the sterilization procedure.

33. A method for testing the effectiveness of a sterilization procedure, the method comprising:
providing a sterilization indicator comprising:
a carrier;
biological material comprising a source of an active enzyme, wherein the source of active enzyme is supported by the carrier; wherein the active enzyme has an enzyme activity that is correlated with the survival of at least one test microorganism commonly used to monitor the effectiveness of a sterilization procedure; wherein the source of an active enzyme is inactivated by a sterilization procedure that is lethal to the test microorganism, but wherein the source of an active enzyme is not inactivated by a sterilization procedure that is sublethal to the test microorganism;
wherein one or more components of the sterilization indicator retains residual oxidizing sterilant;
a neutralizer disposed within the indicator in an amount effective to neutralize residual oxidizing sterilant, wherein the neutralizer is not an enzyme and not a metal catalyst; and
an enzyme substrate that reacts with the active enzyme to form an enzyme-modified product, which has a detectable signal, upon failure of a sterilization procedure;
subjecting the source of active enzyme to a sterilization procedure;
combining the enzyme and the substrate to form an enzyme-modified product;
determining whether the enzyme-modified product, which has a detectable signal, is present or absent; and
correlating the presence of the detectable signal with failure of the sterilization procedure and the absence of the detectable signal with success of the sterilization procedure.

34. The method of embodiment 33, wherein the sterilization indicator is a dual rapid-readout indicator and the source of active enzyme comprises spores of a microorganism that serve as both the source of active enzyme for the enzyme activity test, and the test microorganism for the spore outgrowth test.

35. The method of any one of embodiments 31 through 34, wherein the sterilization procedure uses hydrogen peroxide vapor.

EXAMPLES

Objects and advantages of this disclosure are further illustrated by the following examples, but the particular materials and amounts thereof recited in these examples, as well as other conditions and details, should not be construed to unduly limit this disclosure.

Material and Methods

Spore Preparation

*Geobacillus stearothermophilus* (ATCC 7953) spores used in all Examples were produced on TSA agar plates. The spores were harvested and the pellet washed three times with 4° C. deionized $H_2O$. The spore suspension was centrifuged at 8000 revolutions per minute (rpm) for 15 minutes (min) and the volume of the clean crop was brought to 800 milliliters (mL) by adding sterile deionized $H_2O$. The percentage of transmittance of the spore suspension was measured and recorded ($\lambda$=625 nanometers (nm)).

Spore Carrier Materials

Fourteen different spore carrier materials were tested. These spore carrier materials were all nonwoven samples. All nonwoven materials differed by their chemistry and/or their manufacturing process.

TABLE 1

Spore Carrier Material Description

| Carrier Material | Manufacturer, City/State | Chemistry | Process | Additional information |
|---|---|---|---|---|
| PAPER-591 | Whatman Inc., Piscataway, NJ | Cellulose | | Cellulose based filters used in qualitative analytical techniques. Offers high absorbency and increased wet strength. |
| CRANEGLAS | Crane & Co., Inc., Dalton, MA | Glass-fiber | | CRANEGLAS is made of glass fibers and polymers or high silica glass |
| SX-314 | Ahlstrom, Helsinki Finland | 50% Polyethylene/ 50% Rayon | Spunlace | |
| HEF140-114 | Ahlstrom | Rayon | Spunlace | |
| CEREX PBN | Fiberweb Inc., Old Hickory, TN | Nylon | | Nonwoven fabrics made by spinning and thermally bonding continuous filaments of nylon into textile like fabric |
| TO505 | Fiberweb Inc. | Polypropylene | spunbond-meltblown-spunbond | Nonwoven SMS used in carpet and landscape industry |
| SOFTEX | Fiberweb Inc. | Polythene/ Nylon | Spunbond/ Point bonded | Coextrusion technology for the production of Bico- and Trico-monofilaments; Twin screw technology for high end monofilaments and artificial grass |
| 40AA0 | Polymer Group Inc., Waynesboro, VA | Polypropylene | Carded/ Ultrasonic pin bond | |
| SB3396018 | First Quality Nonwovens Inc., Hazelton, PA | Polypropylene | | Nonwoven Spunbond fabrics feature multi layer webs of excellent uniformity |
| UHF-50 | Kanobo Ltd, Tokyo, Japan | Polyurethane | Spunbond | |
| DOODLE DUSTER | 3M Co., St. Paul, MN | 60% Polypropylene 40% Polyester | Blown Microfiber/ Embossed | Extruder Polypropylene resin |
| SRF2732A-1 | Sage Products Inc., Gary, IL | Polypropylene | Carded/ Needle-punched | |
| UNILAYER | Midwest Filtration Co., Cincinnati, OH | Polypropylene | Spunbond/ Ultrasonic pin bond | Nonwoven, 100% Polypropylene (Layered) |
| UNIPRO 125 | Midwest Filtration Co. | Polypropylene | Spunbond/ Point bonded | Nonwoven, 100% Polypropylene (air permeability; 390 cfm/ft$^2$) |

Processing of Spore Carrier Material to Achieve 3D Porous Carrier

Figure 9A:
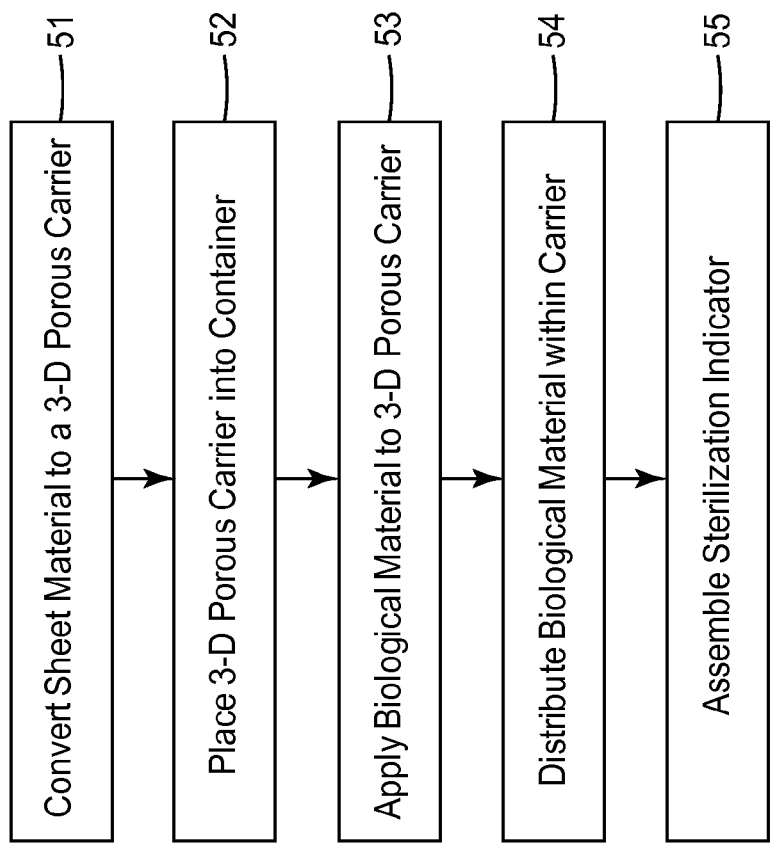
FIG. 9a is a flow diagram of an exemplary method for making a three-dimensional porous carrier of the disclosure and adding biological material (e.g., spores) to the three-dimensional porous carrier so it is distributed within the carrier.

In order to facilitate hydrogen peroxide penetration and removal, each nonwoven sample was blended in a laboratory blender (Waring Commercial, CN) to obtain a three-dimensional (3D) porous carrier. About 1.6 cubic centimeters (cm$^3$) of a three-dimensional porous carrier was used to fill the bottom part of a polypropylene sleeve (diameter=0.8 cm). The process transforming all nonwoven samples into a three-dimensional porous carrier material is illustrated in FIG. 9a.

Spore Coating Process and Assembly of Biological Indicators

Dilutions were made in order to obtain 72% transmittance of *Geobacillus stearothermophilus* spore suspension. To improve the coating process, 360 microliters (μL) of a 30-times diluted spore suspension was applied to 1.6 cm$^3$ of a three-dimensional porous carrier. The sleeves were squeezed to enhance the liquid absorption effect and to enable an even spore coating. The sleeves containing the coated spores distributed within the blended 3D porous carrier materials were incubated for 16 hours (overnight) at 58° C. The biological indicators were assembled by using components of 3M ATTEST 1292 Biological Indicator (available from 3M Company of St. Paul, Minn.), except that the spore-coated porous carriers listed above were used in place of the paper spore strip. The other components such as the 1292 media ampoule, barrier, and perforated cap were also used.

Example 1

Hydrophobicity

Contact Angle Measurement

The hydrophobicity of the nonwoven sheet materials was determined by water contact angle measurement. Contact angle is a quantitative measure of the wetting of a spore carrier material in a sheet format by water. It is defined geometrically as the angle formed by a liquid at the three phase boundary where a liquid, gas and solid intersect. A contact angle of 180° represents a completely hydrophobic surface. A contact angle of near 0° represents a hydrophilic surface. An amount of 10-20 microliters (μL) of a sessile water droplet was applied to the surface of each unblended nonwoven sheet material. The hydrophobicity of the nonwoven sheet materials was determined by water contact angle measurement (Table 2). Based upon the contact angle results, the carrier materials were classified into two groups. The first group of carrier materials was characterized as hydrophilic with their contact angle equal to zero (Paper-591, CRANEGLAS, SX-314 and HEF140-114). The second group was hydrophobic with their contact angle higher or equal to 30° (CEREX PBN, TO505, SOFTEX, 40AA0, SB3396018, UHF-50, DOODLE DUSTER, SRF2732A-1, UNILAYER, UNIPRO 125).

TABLE 2

Contact Angle of Carrier Material

| Carrier material | Contact angle (°) |
|---|---|
| PAPER-591 | 0 ± 0 |
| CRANEGLAS | 0 ± 0 |
| SX-314 | 0 ± 0 |
| HEF140-114 | 0 ± 0 |
| CEREX PBN | 30 ± 8 |
| TO505 | 101 ± 6 |
| SOFTEX | 104 ± 6 |
| 40AA0 | 113 ± 4 |
| SB3396018 | 119 ± 3 |
| UHF-50 | 121 ± 3 |
| DOODLE DUSTER | 121 ± 4 |
| SRF2732A-1 | 123 ± 3 |
| UNILAYER | 124 ± 4 |
| UNIPRO 125 | 126 ± 2 |

Example 2

Effective Fiber Diameter (EFD) and Solidity (%) Determination of the Carrier Material The pressure drop (ΔP) was measured at a volumetric air flow rate of 15 liters per minute using a differential pressure flowmeter (available from TSI Inc., St. Paul, Minn.). For each ΔP measurement a given basis weight of the carrier material sample (each material processed/blended as described above) was packed into a plastic tube with an inner diameter of 7 mm, to form a plug of material 4 mm in height. One end of the plastic tube was open to atmospheric pressure and the other end to a vacuum pump used to establish a constant volumetric air flow rate through the plug of carrier material. The differential pressure flowmeter resided in the path connecting the plastic tube to the vacuum pump. A scrim layer with large openings was used to cap the end of the plastic tube connected to the pump, in order to hold the carrier material within the tube during the measurement of ΔP. Basis Weight in grams per meter squared (g/m$^2$), Solidity in percent (%), and Effective Fiber Diameter (EFD) were measured and calculated as set forth in C. N. Davies, "The Separation of Airborne Dust and Particles," *Institution of Mechanical Engineers*, London, Proceedings 1B, 1952. The results are presented in Table 3. Both the effective fiber diameter and solidity were normalized to the basis weight for comparison. Hydrophilic materials showed a normalized effective fiber diameter comprised between 16-41 micrometers (μm) whereas the EFD for the hydrophobic carriers were between 33-53 μm. The value of the normalized solidity was between 16-33% for the hydrophilic carriers and between 27-36% for the hydrophobic materials.

TABLE 3

Effective Fiber Diameter (EFD) and Solidity (%)

| | | Raw data | | | | Normalized to basis weight | |
|---|---|---|---|---|---|---|---|
| | Carrier material | Basis Weight (g/m$^2$) | ΔP (mm H$_2$O) | EFD (μm) | Solidity (%) | EFD (μm) | Solidity (%) |
| Hydrophilic carrier | CRANEGLAS | 1725 | 1001 | 22 | 22 | 16 | 16 |
| | SX-314 | 1304 | 998 | 31 | 27 | 31 | 27 |
| | HEF140-114 | 1092 | 989 | 18 | 18 | 23 | 22 |
| | PAPER-591 | 1327 | 1055 | 42 | 33 | 41 | 33 |
| Hydrophobic carrier | CEREX PBN | 1436 | 907 | 38 | 30 | 33 | 27 |
| | T0505 | 1457 | 1049 | 60 | 40 | 50 | 36 |
| | SOFTEX | 1431 | 1025 | 49 | 36 | 42 | 33 |
| | 40AA0 | 1402 | 997 | 57 | 39 | 51 | 36 |
| | SB3396018 | 1296 | 1012 | 49 | 36 | 50 | 36 |
| | UHF 50 | 1209 | 982 | 32 | 27 | 36 | 30 |
| | DOODLE DUSTER | 1626 | 1025 | 75 | 45 | 50 | 36 |
| | SRF2372A-1 | 1046 | 929 | 35 | 29 | 53 | 36 |
| | UNILAYER | 1155 | 957 | 41 | 32 | 52 | 36 |
| | UNIPRO 125 | 1055 | 952 | 35 | 29 | 52 | 36 |

Example 3

Residual Hydrogen Peroxide Measurement

This procedure was performed to determine the amount of residual $H_2O_2$ retained by carrier strip materials. The procedure uses the PEROXOQUANT Quantitative Peroxide Assay Kit Number 23280 from Thermo Scientific. The assay detects $H_2O_2$ based on oxidation of ferrous ($Fe^{2+}$) to ferric ion ($Fe^{3+}$) in the presence of xylenol orange. The complex yields a purple product with maximum absorbance at 560 nanometers (nm). A concentration of 10 millimolar (mM) $H_2O_2$ stock solution was diluted to obtain 0.25; 0.2; 0.15; 0.1; 0.05; and 0.001 mM $H_2O_2$. The standard curve is not linear over the entire assay range and it is recommended to use a quadratic or a best-fit curve to obtain the standard points. Five flat carrier strips were used in the experiment (4 samples and 1 control). After transferring the strips to clean tubes, add 1.5 mL. The strips were soaked in the water between 45 minutes to an hour before testing the solution. The dwell time between the sample and working reagent in the cuvette is critical. Depending on how well the carrier material absorbs $H_2O_2$ during sterilization, the dilution factor of the sample solution must be increased or decreased in order to achieve the target of less than 1 unit of absorbance. This ensures greatest accuracy in determining the amount of $H_2O_2$ present on the material.

Data obtained by the PEROXOQUANT Quantitative Peroxide Assay Kit method are presented in Table 4. These data were classified into two category based upon the carrier hydrophobicity. The hydrophilic materials presented $H_2O_2$ retention between 13-273 μg whereas, the hydrophobic carriers retained between 0.03-16.09 μg of $H_2O_2$. The amount of residual hydrogen peroxide is inversely correlated to the carrier hydrophobicity assessed by the contact angle measurement.

TABLE 4

Residual Hydrogen Peroxide

| Carrier material | Residual $H_2O_2$ (μg) |
|---|---|
| PAPER-591 | 13.00 |
| CRANEGLAS | 33.01 |
| SX-314 | 31.71 |
| HEF140-114 | 273.00 |
| CEREX PBN | 16.09 |
| TO505 | 0.55 |
| SOFTEX | 8.87 |
| 40AA0 | 0.70 |
| SB3396018 | 0.85 |
| UHF-50 | 0.23 |
| DOODLE DUSTER | 6.61 |
| SRF2732A-1 | 1.38 |
| UNILAYER | 1.02 |
| UNIPRO 125 | 0.03 |

Example 4

Biological Indicators Exposed to Hydrogen Peroxide in STERRAD Vessel Hydrogen Peroxide Recovery Testing This example compares the effect of residual hydrogen peroxide retained by different hydrophilic and hydrophobic carriers on spore outgrowth. 3M ATTEST 1292 Biological Indicators available from 3M Company, St. Paul, Minn. were modified so that the spore strips were replaced with the 14 different processed (blended) porous spore carrier materials (Table 1). The modified 3M ATTEST 1292 Biological Indicators were steam sterilized to kill the existing spore population. The steam sterilized BIs were then exposed in the back and bottom shelf of a STERRAD 100S hydrogen peroxide/plasma sterilization cycle. Immediately following the hydrogen peroxide/plasma sterilization, a spore suspension; containing approximately $1 \times 10^2$; $1 \times 10^3$; or $1 \times 10^5$ *Geobacillus stearothermophilus* spores; was pipetted onto the carrier material in each BI. Three BIs per carrier material were tested with each spore suspension. Subsequently, the ampule of growth medium was crushed in each BI and all of the BI's were incubated at 60° C. (+/−2° C.). After 24 hours of incubation, each BI was observed for an indication of growth (i.e., a pH change that turned the pH indicator in the medium from purple to yellow).

The effect of residual hydrogen peroxide on BI performance is shown in Table 5. The results are expressed as number of BI growth positive out of 3 BI tested for each concentration. The data can be classified into two groups. The first group contains carrier materials that are all hydrophilic; this group of carrier materials shows no growth after the uncoated BIs were exposed to the $H_2O_2$ (CRANEGLAS, SX-314, HEF140-114, and Paper-591). The growth inhibition observed might be due the presence of residual hydrogen peroxide. The second group of carrier materials included hydrophobic materials. These materials did not inhibit spore growth after the exposure to hydrogen peroxide (CEREX PBN, TO505, SOFTEX, 40AA0, SB3396018, UHF-50, SRF2732A-1, UNILAYER, UNIPRO 125). The data suggest that there is a relationship between the $H_2O_2$ retention and the hydrophilicity of the carrier material. The hydrophobicity, residual hydrogen peroxide and BI performance data presented in Table 5 shows that, in general, there was no inhibition of spore growth when hydrophobic materials were used in the spore carrier.

TABLE 5

Hydrophobicity, Residual $H_2O_2$ Retention and BI Performance

| | Carrier material | Contact Angle (°) | Residual $H_2O_2$ (μg) | Positive BI's/Total BI's Tested (Spore population per BI) ($10^5$) | ($10^3$) | ($10^2$) |
|---|---|---|---|---|---|---|
| Hydrophilic carrier | CRANEGLAS | 0 ± 0 | 13.00 | 0/3 | 0/3 | 0/3 |
| | SX-314 | 0 ± 0 | 33.01 | 0/3 | 0/3 | 0/3 |
| | HEF140-114 | 0 ± 0 | 31.71 | 0/3 | 0/3 | 0/3 |
| | PAPER-591 | 0 ± 0 | 273.00 | 0/3 | 0/3 | 0/3 |
| Hydrophobic carrier | CEREX PBN | 30 ± 8 | 16.09 | 3/3 | 3/3 | 3/3 |
| | T0505 | 101 ± 6 | 0.55 | 3/3 | 3/3 | 3/3 |
| | SOFTEX | 104 ± 6 | 8.87 | 3/3 | 3/3 | 3/3 |
| | 40AA0 | 113 ± 4 | 0.70 | 3/3 | 3/3 | 3/3 |
| | SB3396018 | 119 ± 3 | 0.85 | 3/3 | 3/3 | 3/3 |
| | UHF 50 | 121 ± 3 | 0.23 | 3/3 | 3/3 | 3/3 |
| | DOODLE DUSTER | 121 ± 4 | 6.61 | 0/3 | 0/3 | 0/3 |
| | SRF2372A-1 | 123 ± 3 | 1.38 | 3/3 | 3/3 | 3/3 |
| | UNILAYER | 124 ± 4 | 1.02 | 3/3 | 3/3 | 3/3 |
| | UNIPRO 125 | 126 ± 2 | 0.03 | 3/3 | 3/3 | 3/3 |

Example 5

Biological Indicator Performance Testing-Growth Readout (24 Hours)

This example compares the performance of different hydrophilic and hydrophobic carriers. Dilutions were made in order to obtain 72% transmittance of *Geobacillus stearo-* thermophilus spore suspension ($3 \times 10^6$ spores/ml). To improve the coating process, 360 microliters (μL) of a 30-times diluted spore suspension was used to coat about 1.6 cm³ of a three-dimensional porous carrier. The sleeves containing the coated spores distributed within the blended 3D porous carrier materials were incubated for 16 hours (overnight) at 58° C. The biological indicators were assembled by using components of 3M ATTEST 1292 Biological Indicator (available from 3M Company of St. Paul, Minn.), except that the spore-coated porous carriers listed above were used in place of the paper spore strip. The other components, such as the 1292 media ampoule, and perforated cap were also used.

All biological indicators (BIs) were tested using a 100 GMP STERRAD vessel (Advanced Sterilization Products, CA). The BI (biological indicator) samples were tested in the back and bottom shelf of the 100 GMP STERRAD vessel. These BIs were exposed to hydrogen peroxide vapor from 10 seconds to 8 min (half cycle). A volume of 1.8 mL of 59% $H_2O_2$ was injected in the STERRAD vessel chamber through a septum for each cycle tested. The biological indicator ampoules were activated (crushed) and the BIs were then incubated and observed for 24 hour-growth readout, as described in Example 4.

Data obtained from $H_2O_2$ BIs exposed at different times in the STERRAD vessel are presented in Table 6. The results are expressed as number of BI growth positive out of 5 BI tested for each cycle. The spores coated on hydrophilic carrier materials displayed inconsistent responses to varying hydrogen peroxide exposures. Whereas the hydrophilic materials (CRANEGLAS, SX-314 and HEF140-114) contain either one or two types of cycles or an unusual trend (kill before fractional cycle) (Paper-591).

TABLE 6

BI Performance-Growth Readout (24 hours)

| Carrier material | | Positive BI's/Total BI's Tested | | | | |
|---|---|---|---|---|---|---|
| | | 10 sec | 1 min | 5 min | 6 min | 8 min |
| Hydrophilic carrier | CRANEGLAS | NT | 5/5 | NT | 5/5 | 5/5 |
| | SX-314 | NT | 0/5 | NT | 0/5 | 0/5 |
| | HEF140-114 | NT | 1/5 | NT | 0/5 | 0/5 |
| | PAPER-591 | NT | 5/5 | NT | 0/5 | 4/5 |
| Hydrophobic carrier | CEREX PBN | NT | 5/5 | NT | 5/5 | 5/5 |
| | T0505 | 5/5 | 2/5 | 2/5 | NT | 0/5 |
| | SOFTEX | NT | 5/5 | NT | 5/5 | 5/5 |
| | 40AA0 | 5/5 | 2/4 | 0/5 | NT | 0/5 |
| | SB3396018 | 5/5 | 3/5 | 0/5 | NT | 0/5 |
| | UHF 50 | NT | 5/5 | NT | 5/5 | 5/5 |
| | DOODLE DUSTER | 5/5 | 5/5 | 0/5 | NT | 0/5 |
| | SRF2372A-1 | 5/5 | 5/5 | 0/5 | NT | 0/5 |
| | UNILAYER | 5/5 | 2/5 | 0/5 | NT | 0/5 |
| | UNIPRO 125 | 5/5 | 3/5 | 1/5 | NT | 0/5 |

NT = Not Tested

Example 6

Growth Readout Reliability

Data from the BI growth readout reliability is presented in Table 7. This experiment was performed to investigate the daily readout reliability. These data show a reliable growth response from the first day to the seventh day, no matter the hydrophobicity of the carrier material.

TABLE 7

Growth Readout Reliability from Day 1 to Day 7 (1 min exposure)

| | Carrier material | Growth readout | | | |
|---|---|---|---|---|---|
| | | Day-1 | Day-3 | Day-5 | Day-7 |
| Hydrophilic Carrier | CRANEGLAS | 5/5 | 5/5 | 5/5 | 5/5 |
| | SX-314 | 0/5 | 0/5 | 3/5 | 3/5 |
| | HEF140-114 | 1/5 | 1/5 | 1/5 | 1/5 |
| | PAPER-591 | 5/5 | 5/5 | 5/5 | 5/5 |
| Hydrophobic Carrier | CEREX PBN | 5/5 | 4/5 | 4/5 | 4/5 |
| | T0505 | 2/5 | 2/5 | 2/5 | 2/5 |
| | SOFTEX | 5/5 | 5/5 | 5/5 | 5/5 |
| | 40AA0 | 2/4 | 2/4 | 2/4 | 2/4 |
| | SB3396018 | 3/5 | 3/5 | 3/5 | 3/5 |
| | UHF 50 | 5/5 | 5/5 | 5/5 | 5/5 |
| | DOODLE DUSTER | 5/5 | 5/5 | 5/5 | 5/5 |
| | SRF2372A-1 | 5/5 | 5/5 | 5/5 | 5/5 |
| | UNILAYER | 2/5 | 2/5 | 2/5 | 2/5 |
| | UNIPRO 125 | 3/5 | 3/5 | 3/5 | 3/5 |

Example 7

Correlation Fluorescence/Growth

The correlation between 8 hour-fluorescence and 24 hour-growth readout is presented in Table 8. These results show that 8 hydrophobic porous carrier materials out of the 10 display 100% correlation between fluorescence and growth. In contrast, of the porous hydrophilic type of material, only 2 carriers out of 4 are 100% correlated.

TABLE 8

Correlation Fluorescence/Growth

| | Carrier material | Correlation | |
|---|---|---|---|
| | | Fluor (<8 hours) | Growth (Day-7) |
| Hydrophilic Carrier | CRANEGLAS | 5/5 | 5/5 |
| | SX-314 | 5/5 | 3/5 |
| | HEF140-114 | 2/5 | 1/5 |
| | PAPER-591 | 5/5 | 5/5 |
| Hydrophobic Carrier | CEREX PBN | 0/5 | 4/5 |
| | T0505 | 1/5 | 2/5 |
| | SOFTEX | 5/5 | 5/5 |
| | 40AA0 | 2/4 | 2/4 |
| | SB3396018 | 3/5 | 3/5 |
| | UHF 50 | 5/5 | 5/5 |
| | DOODLE DUSTER | 5/5 | 5/5 |
| | SRF2372A-1 | 5/5 | 5/5 |
| | UNILAYER | 2/5 | 2/5 |
| | UNIPRO 125 | 3/5 | 3/5 |

Example 8

Remediation of Residual Hydrogen Peroxide Spore Recovery Method

About 1.6 cm³ of uncoated (without spores) three-dimensional porous carrier of each type of the sample was assembled in a BI configuration. The uncoated BIs were all exposed for 8 minutes to hydrogen peroxide vapor using a 100 GMP STERRAD vessel. After exposure to hydrogen peroxide vapor, the BIs were disassembled and the carrier material was then coated using different dilution factor in order to obtain $10^2$; $10^3$; and $10^5$ spores per BI. To test the spore recovery ability 50 μL of 1 gram per liter (g/L) of sodium thiosulfate ($Na_2S_2O_3$) was added to each BI. The BI were reassembled, cracked and incubated for 8 hour-fluorescence and 24 hour-growth readout.

This experiment showed the remediation of residual hydrogen peroxide using a "neutralizer" (sodium thiosulfate). After addition of 50 μL of 1 g/L of sodium thiosulfate, all the BI from all the carrier materials are growth positive no matter their hydrophobicity. The results in Table 9 are expressed as number of BI growth positive out of 3 BI tested for each concentration. The results show that sodium thiosulfate used in a specified condition is a good spore recovery agent. These results suggested that if a hydrophilic carrier material is used in a BI designed for hydrogen peroxide sterilization a recovery agent such as sodium thiosulfate should be used to remove the residual hydrogen peroxide. A hydrophobic carrier helps to eliminate or significantly reduce the residual $H_2O_2$.

TABLE 9

Remediation of Residual Hydrogen Peroxide

| | Carrier material | Spore population per BI | | |
|---|---|---|---|---|
| | | $10^5$ | $10^3$ | $10^2$ |
| Hydrophilic carrier | CRANEGLAS | 3/3 | 3/3 | 3/3 |
| | SX-314 | 3/3 | 3/3 | 3/3 |
| | HEF140-114 | 3/3 | 3/3 | 3/3 |
| | PAPER-591 | 3/3 | 3/3 | 3/3 |
| Hydrophobic carrier | CEREX PBN | 3/3 | 3/3 | 3/3 |
| | T0505 | 3/3 | 3/3 | 3/3 |
| | SOFTEX | 3/3 | 3/3 | 3/3 |
| | 40AA0 | 3/3 | 3/3 | 3/3 |
| | SB3396018 | 3/3 | 3/3 | 3/3 |
| | UHF 50 | 3/3 | 3/3 | 3/3 |
| | DOODLE DUSTER | 3/3 | 3/3 | 3/3 |
| | SRF2372A-1 | 3/3 | 3/3 | 3/3 |
| | UNILAYER | 3/3 | 3/3 | 3/3 |
| | UNIPRO 125 | 3/3 | 3/3 | 3/3 |

Example 9

Carrier Material Spatial Format and Effect on BI performance

To better understand the hydrophobicity effect of the carrier on the hydrogen peroxide retention and BI performance, a wetting agent (SILWET 77; Union Carbide Corporation, Danbury, Conn.) was used to alter the surface properties. Two hydrophobic materials (T0505 and UNIPRO 125) were selected and made hydrophilic. Both T0505 and UNIPRO 125 carriers were tested in 2D (two-dimensional or sheet format) and in 3D (three-dimensional porous format). BIs were assembled and tested at 3 different exposure times (Table 10). The spore resistance decreasing when exposure times increase, is observed only when both hydrophobic carriers in 3D porous format are not treated by the wetting agent. This indicates that the hydrophobicity and the carrier configuration play a role in the BI performance.

TABLE 10

Effect of Hydrophobicity Alteration and Carrier Format on BI Performance

| Carrier Material | Carrier Format | Control (hydrophobic carrier) | | | Wetting agent applied (Carrier made hydrophilic) | | |
|---|---|---|---|---|---|---|---|
| | | 3 min | 6 min | 8 min | 3 min | 6 min | 8 min |
| T0505 | 2-D | 0/4 | 0/4 | 0/4 | 1/4 | 0/4 | 1/4 |
| | 3D | 3/4 | 2/4 | 0/4 | 1/4 | 0/4 | 0/4 |
| UNIPRO 125 | 2-D | 0/4 | 0/4 | 0/4 | 0/4 | 2/4 | 0/4 |
| | 3D | 3/4 | 2/4 | 1/4 | 0/4 | 0/4 | 0/4 |

Example 10

Carrier Material Spatial Format and Effect of Residual Hydrogen Peroxide

Table 11 presents the BI performance data when hydrophilic carriers are used in 2D or 3D format and with or without a neutralizer, sodium thiosulfate. The data show more growth positives were detected when the neutralizer was added to the BI's.

TABLE 11

Effect of Residual $H_2O_2$ Remediation and Carrier Format on BI Performance

| Carrier Material | Carrier Format | Without Neutralizer | | | With Neutralizer | | |
|---|---|---|---|---|---|---|---|
| | | 3 min | 6 min | 8 min | 3 min | 6 min | 8 min |
| CRANEGLAS | 2-D | 4/4 | 4/4 | 0/4 | 4/4 | 4/4 | 3/4 |
| | 3D | 4/4 | 4/4 | 4/4 | 4/4 | 4/4 | 4/4 |
| HEF140-114 | 2-D | 0/4 | 4/4 | 0/4 | 4/4 | 4/4 | 1/4 |
| | 3D | 4/4 | 0/4 | 0/4 | 4/4 | 4/4 | 4/4 |

Example 11

Application to Steam Sterilization

The spore crop concentration was adjusted to obtain 67% transmittance. Sorbitol at 10% was added to the coating solution. The spores were coated on the selected porous materials shown in Table 12 and incubated. Then biological indicators were assembled as described in the Spore Coating Process and Assembly of Biological Indicators section above, using these spore-coated porous materials. For each sample, 4 BIs per cycle were exposed to the steam for 7, 11, and 15 minutes at the 121° C. gravity. The BIs were tested in a steam BIER vessel (Joslyn Model No. SB-001 sterilizer, Joslyn Sterilizer Corporation, Farmington, N.Y.). The BIs were activated (cracked) and incubated for 3 hour-fluorescence readout and 24 hour-growth readout.

The BIs were tested in the same condition like the commercially available 1292 steam rapid readout Biological Indicators using a 290 AutoReader, available from 3M Co. Table 12 shows spore resistance decreasing when exposure time increases, when HEF140-114, T0505 and Unilayer are used, demonstrating that this invention can be used with Steam as the sterilant.

TABLE 12

Biological Indicator Performance in Steam Sterilization

| Carrier material | Growth readout | | |
|---|---|---|---|
| | 7 Min | 11 Min | 15 Min |
| HEF140-114 (Hydrophilic) | 4/4 | 4/4 | 1/4 |
| CEREX PBN (Hydrophobic) | 4/4 | 4/4 | 4/4 |
| T0505 (Hydrophobic) | 4/4 | 2/4 | 0/4 |
| UNILAYER (Hydrophobic) | 4/4 | 4/4 | 1/4 |

Example 12

Application to Ethylene Oxide Sterilization

The spore crop concentration was adjusted to obtain 15% transmittance. 7% sorbitol was added to the coating solution. The spores were coated, incubated and assembled as described in the Spore Coating section, above. For each sample, 4 BI per cycle were exposed to the ethylene oxide gas for 17, 24, and 30 min using the Oxyfume Cycle. The BIs were tested in an ethylene oxide BIER vessel (Joslyn Model No. EB-001 sterilizer, Joslyn Sterilizer Corporation, Farmington, N.Y.). The BIs were cracked and incubated for 4 hour-fluorescence and 24 hour-growth readout.

BIs were tested in the same condition like the commercially available 1294 Ethylene Oxide rapid readout Biological Indicators. Table 13 shows spore resistance decreasing when exposure time increases, when HEF140-114, T0505 and Unilayer are used, demonstrating that this invention can be used with EO as the sterilant.

TABLE 13

Biological Indicator Performance in Ethylene Oxide Sterilization

| Carrier material | Growth readout | | |
|---|---|---|---|
| | 17 Min | 24 Min | 30 Min |
| HEF140-114 (Hydrophilic) | 4/4 | 0/4 | 0/4 |

TABLE 13-continued

Biological Indicator Performance in Ethylene Oxide Sterilization

| Carrier material | Growth readout | | |
|---|---|---|---|
| | 17 Min | 24 Min | 30 Min |
| CEREX PBN (Hydrophobic) | 4/4 | 4/4 | 4/4 |
| T0505 (Hydrophobic) | 4/4 | 2/4 | 1/4 |
| UNILAYER (Hydrophobic) | 4/4 | 4/4 | 1/4 |

Example 13

Various Hydrogen Peroxide Neutralizers

This example compares the neutralization effectiveness of different additives in the biological indicators recovery medium. The additives (neutralizers) were added to the recovery media used in the 3M ATTEST 1292 Rapid Readout Biological Indicators. Catalase, L-cysteine, sodium thiosulfate, D-ethionine, S-methyl-cysteine, S-benzyl-L-cysteine, thiodiproprionic acid, potassium ferricyanide and sodium pyruvate were all purchased from Sigma-Aldrich Corporation, St. Louis, Mo. Isoascorbic acid was purchased from Alfa Aesar, Ward Hill, Mass. Methionine was purchased from Calbiochem, EMD Chemicals, Gibbstown, N.J.

3M ATTEST 1292 Biological Indicators were steam sterilized to kill the existing spore population. Two sets of 3M ATTEST 1292 BIs were evaluated, one set contained the paper spore carrier used in the commercially available indicator. In the second set, the spore carrier was replaced with fiberglass strips, commercially available as CRANEGLAS 230-11.0 (Crane &Co., Inc., Dalton, Mass.). The steam sterilized BIs were then exposed in a STERRAD 100S hydrogen peroxide/plasma sterilization cycle. Immediately following the hydrogen peroxide/plasma sterilization, the BIs containing media with and without additives were inoculated with less than 100 Geobacillus stearothermophilus spores recovered from a 3M ATTEST 1292 BI spore strip. The indicators were incubated at 60° C. (+/−2° C.) for 7 days and observed for growth, indicated by a color change from purple to yellow. A positive and negative control was tested for each additive. The positive controls were steam sterilized and inoculated with less than 100 spores. The negative controls were steam sterilized. The results are summarized in the Table 14, below.

TABLE 14

Effective Hydrogen Peroxide Neutralizers

| Neutralizer Additive | Conc. g/l | No. Tested Paper | No. Pos. Paper | No. Tested CRANE-GLAS | No. Pos. CRANE-GLAS | Positive Control | Negative Control |
|---|---|---|---|---|---|---|---|
| Media Only[1] | 0 | 3 | 0 | 4 | 0 | Pos | Neg |
| Catalase[2] | * | 3 | 3 | 4 | 4 | Pos | Neg |
| Isoascorbic acid | 1 | 3 | 3 | 4 | 0 | Pos | Neg |
| Isoascorbic acid | 2 | 3 | 3 | 4 | 4 | Pos | Neg* |
| Isoascorbic acid | 4 | 3 | 3 | 4 | 4 | Pos* | Neg* |
| Isoascorbic acid | 8 | 3 | 3 | 4 | 4 | Pos* | Neg* |
| L-cysteine | 1 | 3 | 1 | 4 | 4 | Pos | Neg |
| L-cysteine | 2 | 3 | 0 | 4 | 4 | Pos | Neg |
| L-cysteine | 4 | 3 | 3 | 4 | 4 | Pos | Neg |
| L-cysteine | 8 | 3 | 3 | 4 | 4 | Pos | Neg |
| Methionine | 1 | 3 | 0 | 4 | 4 | Pos | Neg |
| Methionine | 2 | 3 | 0 | 4 | 4 | Pos | Neg |
| Methionine | 4 | 3 | 3 | 4 | 4 | Pos | Neg |
| Methionine | 8 | 3 | 3 | 4 | 4 | Pos | Neg |
| Sodium thiosulfate | 1 | 3 | 3 | 4 | 4 | Pos | Neg |
| Sodium thiosulfate | 2 | 3 | 3 | 4 | 4 | Pos | Neg* |

TABLE 14-continued

Effective Hydrogen Peroxide Neutralizers

| Neutralizer Additive | Conc. g/l | No. Tested | No. Pos. Paper | No. Tested | No. Pos. CRANE-GLAS | Positive Control | Negative Control |
|---|---|---|---|---|---|---|---|
| Sodium thiosulfate | 4 | 3 | 3 | 4 | 4 | Pos | Neg* |
| Sodium thiosulfate | 8 | 3 | 3 | 4 | 4 | Pos | Neg* |
| D-ethionine | 1 | 3 | 2 | 4 | 4 | Pos | Neg |
| D-ethionine | 2 | 3 | 0 | 4 | 4 | Pos | Neg |
| D-ethionine | 4 | 3 | 2 | 4 | 4 | Pos | Neg |
| D-ethionine | 8 | 3 | 3 | 4 | 4 | Pos | Neg |
| S-methyl-cysteine | 1 | 3 | 0 | 4 | 4 | Pos | Neg |
| S-methyl-cysteine | 2 | 3 | 0 | 4 | 4 | Pos | Neg |
| S-methyl-cysteine | 4 | 3 | 2 | 4 | 4 | Pos | Neg |
| S-methyl-cysteine | 8 | 3 | 3 | 4 | 4 | Pos* | Neg |
| Potassium ferricyanide | 1 | 3 | 3 | 4 | 4 | Pos* | Neg |
| Potassium ferricyanide | 2 | 3 | 3 | 4 | 4 | Pos* | Neg |
| Potassium ferricyanide | 4 | 3 | 3 | 4 | 4 | Pos* | Neg |
| Potassium ferricyanide | 8 | 3 | 3 | 4 | 4 | Pos* | Neg |
| S-benzyl-L-cysteine | 1 | 3 | 0 | 4 | 4 | Pos | Neg |
| S-benzyl-L-cysteine | 2 | 3 | 0 | 4 | 4 | Pos | Neg |
| S-benzyl-L-cysteine | 4 | 3 | 0 | 4 | 4 | Pos | Neg |
| Thiodiproprionic acid | 1 | 3 | 0 | 3 | 1 | Pos | Neg |
| Thiodiproprionic acid | 2 | 3 | 0 | 3 | 3 | Neg$^3$ | Neg |
| Thiodiproprionic acid | 4 | 3 | 0 | 3 | 3 | Neg$^3$ | Neg |
| Thiodiproprionic acid | 8 | 3 | 3 | 3 | 3 | Pos | Neg |
| Sodium pyruvate | 1 | 3 | 0 | NT | NT | Pos | Neg |
| Sodium pyruvate | 2 | 3 | 2 | NT | NT | Pos | Neg |
| Sodium pyruvate | 4 | 3 | 3 | NT | NT | Pos | Neg |
| Sodium pyruvate | 8 | 3 | 3 | NT | NT | Pos | Neg |

Media Only$^1$ - no neutralizers added
Catalase$^2$ - 226 units added per vial
Neg$^3$ - positive control did not grow
Pos*/Neg* - positive (yellow) or negative (purple) was discolored by the additive The data in the above Table 14 shows with media only (no neutralizer), the residual hydrogen peroxide with both the paper and fiberglass carriers inhibited the outgrowth of the spores. The addition of catalase to the media sufficiently neutralized the residual hydrogen peroxide and allowed the spores to grow and change the pH indicator from purple to yellow. The fiberglass carriers retain less residual hydrogen peroxide than the paper carriers and effectively neutralized the hydrogen peroxide with 1-2 grams of additive per liter. Only isoascorbic acid, sodium thiosulfate and the potassium ferricyanide effectively neutralized the paper carriers at the 1 gram per liter levels. All of the other neutralizer additives, except for s-benzyl-L-cysteine, neutralized the paper carriers at concentrations of 4-8 grams per liter. The s-benzyl-L-cysteine was not soluble at 8 grams per liter. The pH indicator color was affected by some levels of isoascorbic acid, sodium thiosulfate, s-methyl-cysteine and potassium ferricyanide. This example demonstrates all the additives tested can effectively neutralize hydrogen peroxide and are compatible with the growth of G. stearothermophilus.

The complete disclosures of the patents, patent documents, and publications cited herein are incorporated by reference in their entirety as if each were individually incorporated. Various modifications and alterations to this disclosure will become apparent to those skilled in the art without departing from the scope and spirit of this disclosure. It should be understood that this disclosure is not intended to be unduly limited by the illustrative embodiments and examples set forth herein and that such examples and embodiments are presented by way of example only with the scope of the disclosure intended to be limited only by the claims set forth herein as follows.

What is claimed is:

1. A self-contained sterilization indicator for testing the effectiveness of a sterilization procedure, the self-contained sterilization indicator comprising:
   an outer container having at least one opening to allow sterilant to enter the outer container during the sterilization procedure;
   a carrier contained within the outer container;
   biological material comprising a source of an active enzyme, wherein the source of active enzyme is supported by the carrier; wherein the active enzyme has an enzyme activity that is correlated with the survival of at least one test microorganism commonly used to monitor the effectiveness of a sterilization procedure; wherein the source of an active enzyme is inactivated by a sterilization procedure that is lethal to the test microorganism, but wherein the source of an active enzyme is not inactivated by a sterilization procedure that is sublethal to the test microorganism;

wherein one or more components of the sterilization indicator retains residual oxidizing sterilant;

a neutralizer disposed within the indicator in an amount effective to neutralize residual oxidizing sterilant, wherein the neutralizer is not an enzyme and not a metal catalyst; and a breakable inner container within the outer container, wherein the inner container:

is impermeable to the sterilant used in the sterilization procedure;

includes an enzyme substrate; and is adapted so that it may be broken to allow the enzyme substrate to react with active enzyme to form an enzyme-modified product that provides a detectable indication of the failure of a sterilization procedure.

2. The sterilization indicator of claim 1, wherein the neutralizer is a sulfur-containing compound.

3. The sterilization indicator of claim 2, wherein the sulfur-containing compound is selected from the group consisting of methionine, L-cysteine, D-ethionine, S-methyl-L-cysteine, S-benzyl-L-cysteine, sodium thiosulfate, glutathionine, L-cystathionine, N-acetyl-L-cysteine, carboxymethylcysteine, D,L-homocysteine, D,L-homocysteine-thiolactone, thiodipropionic acid, and combinations thereof.

4. The sterilization indicator of claim 1, wherein the neutralizer is a non-sulfur-containing compound.

5. The sterilization indicator of claim 1, wherein the neutralizer is isolated from the sterilant during sterilization.

6. The sterilization indicator of claim 1, wherein the carrier comprises a material in a sheet form.

7. The sterilization indicator of claim 1, wherein the carrier comprises a porous carrier and the biological material is distributed within the carrier.

8. The sterilization indicator of claim 7, wherein the porous carrier occupies at least 5% of the volume of the container in which it is located.

9. The sterilization indicator of claim 7, wherein the porous carrier occupies no more than 50% of the volume of the container.

10. The sterilization indicator of claim 8, wherein the porous carrier has a solidity of greater than 5%.

11. The sterilization indicator of claim 8, wherein the porous carrier has an effective fiber diameter of greater than 10 microns.

12. The sterilization indicator of claim 1, wherein the carrier retains residual oxidizing sterilant.

13. The sterilization indicator of claim 1, wherein the carrier comprises a hydrophobic material.

14. The sterilization indicator of claim 1, wherein the carrier comprises a hydrophilic material.

15. The sterilization indicator of claim 1, wherein the detectable indication of the failure of a sterilization procedure comprises a detectable fluorescence, luminescence, and/or chromogenic indication.

16. The sterilization indicator of claim 1, wherein the oxidizing sterilant comprises hydrogen peroxide vapor.

* * * * *